US010294269B2

(12) United States Patent
Llenas Calvo et al.

(10) Patent No.: US 10,294,269 B2
(45) Date of Patent: May 21, 2019

(54) DIPEPTIDYL KETOAMIDE COMPOUNDS AND THEIR USE FOR THE TREATMENT AND/OR PREVENTION OF FAT ACCUMULATION

(71) Applicant: LANDSTEINER GENMED, S.L.

(72) Inventors: Jesús Llenas Calvo, Seville (ES); Miriam Royo Exposito, Barcelona (ES); Elena Carceller González, Sant Cugat del Valles-Barcelona (ES); Unai Elezcano Donaire, Barcelona (ES); Sergio Rodriguez Escrich, Barcelona (ES); Enrique Vazquez Tatay, Seville (ES)

(73) Assignee: LANDSTEINER GENMED, S.L., Seville (ES)

( * ) Notice: Subject to any disclaimer, the term of this patent is extended or adjusted under 35 U.S.C. 154(b) by 0 days.

(21) Appl. No.: 15/509,107

(22) PCT Filed: Sep. 8, 2015

(86) PCT No.: PCT/EP2015/070504
§ 371 (c)(1),
(2) Date: Mar. 6, 2017

(87) PCT Pub. No.: WO2016/038040
PCT Pub. Date: Mar. 17, 2016

(65) Prior Publication Data
US 2018/0237473 A1 Aug. 23, 2018

(30) Foreign Application Priority Data
Sep. 8, 2014 (EP) ..................... 14382332

(51) Int. Cl.
C07K 5/02 (2006.01)
C07K 5/06 (2006.01)
A61K 38/05 (2006.01)
A61P 3/04 (2006.01)
A61P 3/06 (2006.01)
C07C 237/22 (2006.01)
C07C 271/22 (2006.01)
C07C 275/16 (2006.01)
C07D 211/62 (2006.01)
C07D 213/81 (2006.01)
C07D 213/82 (2006.01)
C07D 215/54 (2006.01)
C07D 217/02 (2006.01)
C07D 237/24 (2006.01)
C07D 239/28 (2006.01)
C07D 241/24 (2006.01)
C07D 309/08 (2006.01)
C07D 317/60 (2006.01)

(52) U.S. Cl.
CPC ................ C07K 5/06 (2013.01); A61K 38/05 (2013.01); A61P 3/04 (2018.01); A61P 3/06 (2018.01); C07C 237/22 (2013.01); C07C 271/22 (2013.01); C07C 275/16 (2013.01); C07D 211/62 (2013.01); C07D 213/81 (2013.01); C07D 213/82 (2013.01); C07D 215/54 (2013.01); C07D 217/02 (2013.01); C07D 237/24 (2013.01); C07D 239/28 (2013.01); C07D 241/24 (2013.01); C07D 309/08 (2013.01); C07D 317/60 (2013.01); C07K 5/0202 (2013.01)

(58) Field of Classification Search
None
See application file for complete search history.

(56) References Cited

U.S. PATENT DOCUMENTS

| 5,514,694 A * | 5/1996 | Powers .............. C07K 5/06043 514/20.2 |
| 5,610,297 A | 3/1997 | Powers |
| 6,686,335 B1 | 2/2004 | Josef et al. |
| 7,060,683 B2 | 6/2006 | Josef et al. |
| 7,491,705 B2 | 2/2009 | Shirasaki et al. |

FOREIGN PATENT DOCUMENTS

| CN | 1319008 A | 10/2001 | |
| WO | WO-9400095 A2 * | 1/1994 | ........... A61K 31/365 |
| WO | 0016767 A1 | 3/2000 | |
| WO | 2005056519 A1 | 6/2005 | |

OTHER PUBLICATIONS

Basso et al. ("Elaboration of Peptidomimetics Derived from a PADAM Approach: Synthesis of Polyfunctionalised 2(1H)-Pyrazinones via an Unexpected Aromatisation," Synlett, 2011, vol. 2011, No. 14, pp. 2009-2012). (Year: 2011).*
Lee-Dutra, Alice, et al.; "Cathepsin S inhibitors: 2004-2010," Expert Opinion on Therapeutic Patents, 2011, pp. 311-337, vol. 21, Issue 3; Abstract Only.
International Preliminary Report on Patentability, dated Dec. 13, 2016.
Ovat, Asli, et al.; "Peptidyl Alpha-Ketoamides with Nucleobases, Methylpiperazine, and Dimethylaminoalkyl Substituents as Calpain Inhibitors," J. Med. Chem., 2010, pp. 6326-6336, vol. 53.
STN Reg Database, Dec. 5, 2011 (disclosing CAS Nos. 1348824-64-5, 944580-61-4, 904299-60-1, 677274-98-5, 181769-50-6, 181769-46-0, 181769-43-7, 178675-73-5, 178675-70-2, 161021-88-1, 161021-87-0, 160868-23-5, 160801-71-8, 160299-89-8, 150519-12-3, 150519-08-7, 145731-46-0, 145731-45-9, 145731-43-7, 145731-40-4, 145731-39-1, 145731-38-0, 145731-36-8, 144248-94-2, 144248-93-1, 144231-83-4, 144237-78-7, 144231-77-6, 144231-76-5, 144231-73-2, 144231-72-1, 261786-31-6, 261786-43-0, 178675-60-0, 178675-59-7).

(Continued)

Primary Examiner — Christina Bradley
(74) Attorney, Agent, or Firm — Tristan A. Fuierer; Olive Law Group, PLLC

(57) ABSTRACT

The present invention relates to the use of dipeptidyl keto-amide compounds for preventing accumulation of triglycerides in adipose tissue or for reducing the amount of triglycerides in adipose tissue in a subject in need thereof and to novel dipeptidyl ketoamide compounds.

24 Claims, No Drawings

(56) References Cited

OTHER PUBLICATIONS

STN Reg Database cont., Dec. 5, 2011 (disclosing CAS Nos. 178675-57-5, 153514-01-3, 153370-97-9, 153370-96-8).
Chinese Office Action, dated Jun. 20, 2018.

* cited by examiner

DIPEPTIDYL KETOAMIDE COMPOUNDS AND THEIR USE FOR THE TREATMENT AND/OR PREVENTION OF FAT ACCUMULATION

CROSS-REFERENCE TO RELATED APPLICATIONS

This application is filed under the provisions of 35 U.S.C. § 371 and claims the priority of International Patent Application No. PCT/EP2015/070504 filed on 8 Sep. 2015 entitled "DIPEPTIDYL KETOAMIDE COMPOUNDS AND THEIR USE FOR THE TREATMENT AND/OR PREVENTION OF FAT ACCUMULATION" in the name of Jesús LLENAS CALVO, et al., which claims priority to European Patent Application No. 14382332.6, filed on 8 Sep. 2014, both of which are hereby incorporated by reference herein in their entirety.

FIELD OF THE INVENTION

The invention relates to the use of dipeptidyl ketoamide compounds for preventing accumulation of triglycerides in adipose tissue or for reducing the amount of triglycerides in adipose tissue in a subject in need thereof. Prevention of triglyceride accumulation and reduction of the amount of triglycerides in adipose tissue allows the use of the dipeptidyl ketoamide compounds of the invention to control weight gain, and/or to treat an obesity-related condition selected from the group consisting of obesity, lipid storage disease (in particular hepatic steatosis) and hyperlipemia. The invention further relates to a subgroup of novel dipeptidyl ketoamide compounds.

BACKGROUND OF THE INVENTION

Adipose tissue or body fat is loose connective tissue composed mostly of adipocytes. In addition to adipocytes, adipose tissue contains the stromal vascular fraction (SVF) of cells including preadipocytes, fibroblasts, vascular endothelial cells and a variety of immune cells (i.e. adipose tissue macrophages (ATMs)). Adipose tissue is derived from preadipocytes. Its main role is to store energy in the form of lipids, although it also cushions and insulates the body. However, excessive accumulation of fat in adipose tissue is undesirable and may lead in first instance to aesthetic problems but ultimately also to pathological conditions such as obesity, lipid storage disease (in particular hepatic steatosis) and hyperlipemia.

The invention relates to the use of dipeptidyl ketoamide compounds for preventing accumulation of triglycerides in adipose tissue or for reducing the amount of triglycerides in adipose tissue in a subject in need thereof. Prevention of triglyceride accumulation and reduction of the amount of triglycerides in adipose tissue allows the use of the dipeptidyl ketoamide compounds of the invention to control weight gain, and/or to treat an obesity-related condition selected from the group consisting of obesity, lipid storage disease (in particular hepatic steatosis) and hyperlipemia.

Thus, the invention also relates to a i) non-therapeutic method for reducing fat accumulation in a subject which does not suffer from obesity or other obesity-related conditions such as lipid storage disease (in particular hepatic steatosis) and hyperlipemia by administration of certain dipeptidyl ketoamide compounds, ii) the use of said dipeptidyl ketoamide compounds for preventing and/or treating an obesity-related condition selected from the group consisting of obesity, lipid storage disease (in particular hepatic steatosis) and hyperlipemia and iii) said dipeptidyl ketoamide compounds for use in preventing and/or treating an obesity-related condition selected from the group consisting of obesity, lipid storage disease (in particular hepatic steatosis) and hyperlipemia.

Obesity is excess body weight for a particular age, sex and height as a consequence of imbalance between energy intake and energy expenditure. The primary cause of obesity is either due to overeating, inadequate exercise or eating disorder, some genetic disorders, underlying illness (e.g., hypothyroidism), certain medications, sedentary lifestyle, a high glycemic diet (i.e., a diet that consists of meals that give high postprandial blood sugar) weight cycling (caused by repeated attempts to lose weight by dieting, eating disorders), stress and insufficient sleep.

A common indication of a person's overweight is the body mass index (BMI) which is a measure of relative weight based on an individual's mass and height and is defined as the individual's body mass divided by the square of their height—with the value universally being given in units of $kg/m^2$.

It is generally accepted within the medical profession that a person does not have overweight if he has a BMI not higher than 25 $kg/m^2$. On the other side when a person's BMI exceeds a value of 30 $kg/m^2$ it is generally accepted that said person is suffering from obesity. Between 25 $kg/m^2$ and 30 $kg/m^2$ the person is considered to have overweight.

Obesity is characterized as uncontrolled adipose tissue mass in the body and recognized as the fastest growing metabolic disorder in the world. An increase in adipose tissue mass can be the result of the production of new fat cells through the process of adipogenesis and/or the deposition of increased amounts of cytoplasmic triglyceride or lipid droplets per cell. Adipogenesis is the process of cell differentiation by which preadipocytes become adipocytes. In the adipogenesis process, proliferation of preadipocytes or precursor fat cells needs to be followed by the differentiation of these cells to the mature adipocyte phenotype. Increased lipid accumulation in the mature adipocyte cells is the most important feature of obesity disorder.

Fat is stored as triglycerides form in adipose tissue. Reducing the formation of new adipose tissue and formation of fat reserves through inhibition of differentiation of preadipocytes into mature adipocytes may be a good strategy to control adipogenesis mediated diseases, especially obesity. Modulation of adipogenesis in humans may thus lead to a reduction in the burden of obesity.

Low-caloric diets and exercise may help with weight loss; however, diet and exercise alone have not proven successful for long-term solutions in weight management. In addition, supplementation with drugs that suppress appetite, reduce food intake, reduce dietary fat absorption, increase energy expenditure and effect nutrient partitioning or metabolism have potential efficacy but they are unfortunately accompanied by adverse side effects (C. A. Haller and N. L. Benowitz., New England J. Medicine, 2000, 343, 1833-1838). Several drugs have been prescribed for the treatment of obesity (M. K. Sharma et al., European Journal of Medicinal Chemistry, 2014, 79, 298-339). One such drug, is phentermine (Fastin, Adipex P), which is prescribed for short term use in weight control. However phentermine has side effects such as high blood pressure, headache, insomnia, irritability and nervousness. Another drug for weight control is Orlistat (marketed as Xenical® by Roche and as Alli® by GlaxoSmithKline). A number of undesirable side effects have also been reported for Orlistat: gas generation, cramps, diarrhoea and elevated blood pressure.

Thus, the need exist to find new drugs to be used in anti-obese therapy.

SUMMARY OF THE INVENTION

The present inventors surprisingly found that certain dipeptidyl ketoamide compounds are capable of reducing adipogenesis and/or the deposition of increased amounts of cytoplasmic triglyceride or lipid droplets in adipocytes, thereby being capable to prevent accumulation of triglycerides in adipose tissue and/or to reduce the amount of triglycerides in adipose tissue in a subject in need thereof, which makes them ideal candidates for the treatment of obesity and other obesity-related conditions selected from the group consisting of lipid storage disease (in particular hepatic steatosis) and hyperlipemia.

In the first aspect, the invention relates to a compound of formula (I):

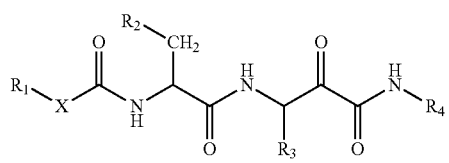

(I)

wherein

X is selected from the group consisting of a single bond, an oxygen atom and a —NH— group, when X is O, $R_1$ is selected from the group consisting of a) $C_{1-8}$-alkyl, optionally substituted by one $C_{1-8}$ alkoxy group, b) $C_{6-10}$-aryl-$C_{1-4}$alkyl and c) $C_{5-10}$heteroaryl-$C_{1-4}$alkyl wherein the $C_{5-10}$heteroaryl rest comprises 1 to 3 heteroatoms selected from the group consisting of nitrogen, oxygen and sulphur, when X is an single bond or a —NH— group, $R_1$ is selected from the group consisting of d) phenyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; e) naphthyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; f) $C_{5-10}$heterocyclyl-$C_{0-2}$alkyl wherein the heterocyclyl rest is saturated or unsaturated and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g) $C_{1-6}$ linear or branched alkyl, optionally substituted by one $C_{1-8}$ alkoxy group and h) $C_{3-6}$cycloalkyl-$C_{0-2}$alkyl optionally substituted by 1 to 3 substituents selected from the group consisting of OH, $NR_5R_6$, CN, $CF_3$, $C_{1-6}$ linear or branched alkyl and halogen atoms;

$R_2$ is selected from the group consisting of i) $C_{1-8}$-alkyl optionally substituted with 1, 2 or 3 fluor atoms, j) $C_{1-8}$-alkoxy-O—$C_{1-8}$-alkyl and k) $C_{3-6}$cycloalkyl-$C_{0-2}$alkyl wherein the cycloalkyl ring is optionally substituted with 1, 2 or 3 fluor atoms;

$R_3$ is selected from the group consisting of l) $C_{1-8}$-alkyl and m) benzyl optionally substituted by 1 to 3 substituents selected from the group consisting of $C_{1-4}$-alkyl, MeO, CN and halogen atoms;

$R_4$ is selected from the group consisting of n) $C_{1-8}$-alkyl, o) $C_{3-6}$cycloalkyl-$C_{0-2}$alkyl optionally substituted by $C_{1-4}$-alkyl and p) $C_{1-8}$-alkoxy; and $R_5$ and $R_6$ are independently selected from the group consisting of hydrogen atoms and $C_{1-6}$ linear or branched alkyl groups;

or a pharmaceutically acceptable salt thereof for use in the treatment and/or prevention of an obesity-related conditions selected from the group consisting of obesity, lipid storage disease (in particular hepatic steatosis) and hyperlipemia.

In a second aspect, the invention relates to the use of a compound of formula (I) as defined in the first aspect or a pharmaceutically acceptable salt thereof for the manufacture of a medicament for the treatment and/or prevention of an obesity-related condition selected from the group consisting of obesity, lipid storage disease (in particular hepatic steatosis) and hyperlipemia.

In a third aspect, the invention relates to a method of treatment and/or prevention of an obesity-related condition selected from the group consisting of obesity, lipid storage disease (in particular hepatic steatosis) and hyperlipemia in a subject in need thereof, which comprises administering to said subject a therapeutically effective amount of a compound of formula (I) as defined in the first aspect or a pharmaceutically acceptable salt thereof.

In a fourth aspect, the invention relates to the non-therapeutic use of a compound of formula (I) as defined in the first aspect
or a pharmaceutically acceptable salt thereof to reduce fat accumulation, for example to improve bodily appearance, in a subject which does not suffer from obesity.

In a fifth aspect, the present invention relates to a compound of formula (II)

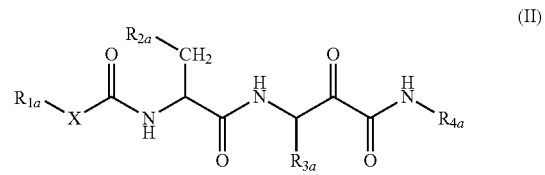

(II)

wherein

X is selected from the group consisting of a single bond, an oxygen atom and a —NH— group, when X is O, $R_{1a}$ is selected from the group consisting of a1) $C_{1-8}$-alkyl, optionally substituted by one $C_{1-8}$ alkoxy group, b1) $C_{6-10}$-aryl-$C_{1-4}$alkyl and c1) $C_{5-10}$heteroaryl-$C_{1-4}$alkyl wherein the $C_{5-10}$heteroaryl rest comprises 1 to 3 heteroatoms selected from the group consisting of nitrogen, oxygen and sulphur, when X is an single bond, $R_{1a}$ is selected from the group consisting of d1) phenyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; f1) $C_{5-10}$heterocyclyl-$C_{0-2}$alkyl wherein the heterocyclyl rest comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g1) $C_{1-6}$ linear or branched alkyl, optionally substituted by one $C_{1-8}$ alkoxy group and h1) $C_{3-6}$cycloalkyl-$C_{0-2}$alkyl optionally substituted by 1 to 3 substituents selected from the group consisting of OH, $NR_{5a}R_{6a}$, CN, $CF_3$, $C_{1-6}$ linear or branched alkyl and halogen atoms;

when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NR_{5a}R_{6a}$, CN, $CF_3$, $C_{1-6}$ linear or branched alkyl and halogen atoms; f2) $C_{5-10}$heterocyclyl-$C_{0-2}$alkyl wherein the heterocyclyl rest comprises 1 to 3 heteroatoms selected from the group consisting of nitrogen, oxygen and sulphur and is optionally substituted by 1 to 3 substituents selected from the group consisting of OH, $NR_{5a}R_{6a}$, CN, $CF_3$, $C_{1-6}$ linear or branched alkyl and halogen atoms; g2) $C_{1-6}$ linear or branched alkyl, optionally substituted by one $C_{1-8}$ alkoxy group and h2) $C_{3-6}$cycloalkyl-$C_{0-2}$alkyl optionally substituted by 1 to 3 substituents selected from the group consisting of OH, $NH_2$, CN, $CF_3$, $C_{1-6}$ linear or branched alkyl and halogen atoms;

$R_{2a}$ is selected from the group consisting of i1) $C_{1-8}$-alkyl optionally substituted with 1, 2 or 3 fluor atoms, j1) $C_{1-8}$-alkoxy-$C_{1-8}$-alkyl and k1) $C_{3-6}$cycloalkyl-$C_{0-2}$alkyl wherein the cycloalkyl ring is optionally substituted with 1, 2 or 3 fluor atoms with the proviso that when X is O then $R_{2a}$ is not an isopropyl group, $R_{3a}$ is selected from the group consisting of l1) $C_{1-8}$-alkyl and m1) benzyl optionally substituted by 1 to 3 substituents selected from the group consisting of $C_{1-4}$-alkyl, MeO, CN and halogen atoms with the proviso that when X is a single bond and $R_{1a}$ is a $C_{5-10}$heterocyclyl-$C_{0-2}$alkyl group, $R_{3a}$ is not an ethyl group;

$R_{4a}$ is selected from the group consisting of n1) $C_{1-8}$-alkyl, o1) $C_{3-6}$cycloalkyl-$C_{0-2}$alkyl optionally substituted by $C_{1-4}$-alkyl and p1) $C_{1-8}$-alkoxy; and $R_{5a}$ and $R_{6a}$ are independently selected from the group consisting of hydrogen atoms and $C_{1-6}$ linear or branched alkyl groups;

or a pharmaceutically acceptable salt thereof.

In a further aspect the present invention relates to a process for the preparation of a compound of formula (I) as defined in the first aspect, in particular of a compound of formula (II) as defined in the fifth aspect, which comprises the reaction of a compound of formula (IV) with Dess-Martin periodinane as shown below

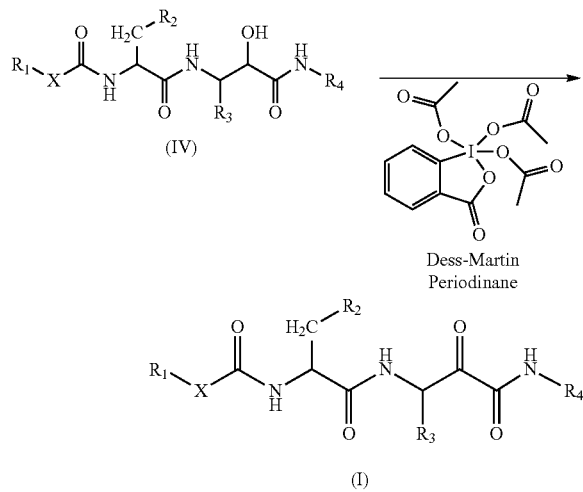

In a further aspect the present invention relates to a pharmaceutical composition comprising a compound of formula (II) as defined in the fifth aspect, or a pharmaceutically acceptable salt thereof, and a pharmaceutically acceptable excipient.

DESCRIPTION OF THE INVENTION

Definitions

Some definitions are included with the aim of facilitating the understanding of the invention.

The term "alkyl" as employed herein alone or as part of another group designates a linear or branched saturated monovalent hydrocarbon chain containing the number of carbon atoms indicated in each case which is typically from of one to six carbon atoms, and preferably from one to three. Examples of alkyls are methyl, ethyl, propyl, 2-propyl, n-butyl, isobutyl, sec-butyl, tert-butyl, n-pentyl, isopentyl, sec-pentyl, tert-pentyl, neopentyl, and the like.

The term "alkoxy" as employed herein alone or as a part of another group designates an alkyl group as defined above linked through oxygen, i.e. alkyl-O—, wherein the alkyl group may be substituted by an aryl group as defined below. Examples of which include methoxy, ethoxy, isopropoxy, tertbutoxy, benzyloxy, and the like.

The term "aryl" means a mono- or bicyclic aromatic group, containing the number of carbon ring atoms indicated in each case which is typically from six to ten, wherein the monocyclic ring is aromatic, and at least one of the rings in the bicyclic ring is aromatic. Representative examples include phenyl, naphthyl, and indanyl, and the like.

The term "aryl" means a mono- or bicyclic aromatic group, containing the number of carbon ring atoms indicated in each case which is typically from six to ten, wherein the monocyclic ring is aromatic, and at least one of the rings in the bicyclic ring is aromatic. Representative examples include phenyl, naphthyl, and indanyl, and the like.

The term "arylalkyl" is used in the present invention to designate and aryl group which is linked to an alkylene group —$(CH_2)_n$—. When the integral n takes a value of zero the arylalkyl group is in fact an aryl group. Similarly, the term "heteroarylalkyl" is used in the present invention to designate and heteroaryl group which is linked to an alkylene group —$(CH_2)_n$— and the term cycloalkylalkyl is used in the present invention to designate and aryl group which is linked to an alkylene group —$(CH_2)_n$—. When the integral n takes a value of zero the heteroarylalkyl group is in fact an heteroaryl group.

The terms "halogen" and "halo" refer to any one of F, Cl, Br and I.

The term "haloalkyl" as employed herein alone or as a part of another group designates an alkyl group as defined above substituted with one or more halogen atoms, preferably one, two, three or four halogen atoms. Examples of which include bromomethyl, chloromethyl, fluoromethyl, trifluoromethyl, 1-bromoethyl, 2-bromoethyl, 1,2-dibromoethyl, 1,1-dibromoethyl, 2,2-dibromoethyl, 1-chloroethyl, 2-chloroethyl, 1,2-dichloroethyl, 1,1-dichloroethyl, 2,2-dichloroethyl, 1-fluoroethyl, 2-fluoroethyl, 1,2-difluoroethyl, 1,1-difluoroethyl, 2,2-difluoroethyl and the like.

The term "heteroaryl" means a monocyclic, 5- to 6-membered monocyclic or 8- to 10-membered bicyclic fused bicyclic ring system containing one to more, specifically one, two or three ring heteroatoms independently selected from O, N and S, and the remaining ring atoms being carbon. The nitrogen and sulfur atoms may be optionally oxidized, and the nitrogen heteroatom is optionally quaternized. In the case of monocyclic heteroaryl groups the ring will be aromatic and in the case of fused bicyclic groups at least one of the fused rings will be aromatic. Examples of heteroaryl groups are pyridinyl, furanyl, thiophenyl, quinolinyl, tetrahydroquinolinyl and the like.

The term "heterocyclyl" means a saturated or unsaturated monocyclic group containing the number of ring atoms indicated in each case with is typically of 3 to 8, preferably 5 to 7, or a saturated or unsaturated fused bicyclic group containing the number of ring atoms indicated in each case with is typically of 5 to 12 ring atoms in which one or more, specifically one, two or three ring heteroatoms are independently selected from N, O, and S. The nitrogen and sulfur atoms may be optionally oxidized, and the nitrogen heteroatom is optionally quaternized. Fused bicyclic radical includes bridged ring systems. Examples of heterocyclyl are morpholinyl, piperidinyl, piperazinyl, pyrrolidinyl, oxolanyl, thiolanyl, oxanyl, thianyl, azepanyl, oxepanyl, tiepanyl, thiomorpholinyl, dioxanyl, dithianyl. The term heterocyclyl also encompasses fully unsaturated heterocyclic groups, i.e. heteroaromatic groups. Examples of heteroaromatic groups are pyridinyl, pyrazinyl, pyridazinyl, piyrimidinyl, pyrrolyl, pyrazolyl, imidazolyl, oxazilyl, isoxazolyl, quinolinyl and isoquinolinyl.

References to substituted groups in the compounds of the present invention refer to the specified moiety that may be substituted at one or more available positions by one or more suitable groups, in particular by one, two or three substituents.

The term "salt" must be understood as any form of a compound according to the present invention, in which said compound is in ionic form or is charged and coupled to a counter-ion (a cation or anion) or is in solution. This definition also includes quaternary ammonium salts. The definition includes in particular pharmaceutically acceptable salts.

The term "pharmaceutically acceptable salt" embraces salts with a pharmaceutically acceptable acid or base, which are synthesized from the parent compound which contains an acidic moiety by addition of a pharmaceutically acceptable base, or which are synthesized from the parent compound which contains a basic moiety by addition of a pharmaceutically acceptable acid. Pharmaceutically acceptable acids include both inorganic acids, for example, hydrochloric, sulfuric, phosphoric, diphosphoric, hydrobromic, hydroiodic, and nitric acid, and organic acids, for example, citric, fumaric, maleic, malic, mandelic, ascorbic, oxalic, succinic, tartaric, benzoic, acetic, methanesulfonic (mesylate), ethanesulfonic, benzenesulfonic (besylate), or p-toluenesulfonic (tosylate) acid. Pharmaceutically acceptable bases include alkali metal (e.g., sodium or potassium) and alkali earth metal (e.g., calcium or magnesium) hydroxides and organic bases, such as alkyl amines, arylalkyl amines, and heterocyclic amines. For instance, pharmaceutically acceptable salts of compounds provided herein are synthesized from the parent compound which contains a basic or an acid moiety by conventional chemical methods. Generally, such salts are, for example, prepared by reacting the free base or free acid forms of these compounds with a stoichiometric amount of the appropriate acid or base, respectively, in water or in an organic solvent or in a mixture of the two.

All stereoisomers of the compounds of this invention are contemplated either alone or as mixtures thereof. The process of preparation can utilize racemates, enantiomers, or diastereomers as starting materials. When diastereomeric or enantiomeric products are prepared, they can be separated by conventional methods, for example, chromatographic or functional crystallization.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

Certain compounds of the present invention can exist in unsolvated forms as well as solvated forms, including hydrated forms. In general, the solvated forms are equivalent to unsolvated forms and are encompassed within the scope of the present invention.

Certain compounds of the present invention may exist in multiple crystalline or amorphous forms. In general, all physical forms are equivalent for the uses contemplated by the present invention and are intended to be within the scope of the present invention.

The term "prevention", as used herein, refers to the administration of a compound of formula (I) or of a compound of formula (II) of the invention in an initial or early stage of a disease or condition, or to also prevent its onset.

The term "treatment" is used to designate the administration of a compound of formula (I) or of a compound of formula (II) of the invention to control disorder progression before or after the clinical signs had appeared. By control of the disorder progression it is meant to designate beneficial or desired clinical results including, but not limited to, reduction of symptoms, reduction of the length of the disorder, stabilization pathological state (specifically avoidance of further deterioration), delay in the disorder's progression, improvement of the pathological state and remission (both partial and total). In a particular embodiment of the invention the compound of formula (I) or of formula (II) of the invention is used to control the disorder progression once at least one of the disorder's clinical signs has appeared.

The term "medicament", as used herein, refers to a pharmaceutical composition of the invention comprising a compound of formula (I) or a compound of formula (II) of the invention. The medicament may be administered by any suitable route. It is prepared by conventional means with pharmaceutically acceptable excipients.

The term "subject", as used herein, refers to any animal or human that is suffering from one of the diseases or conditions disclosed herein. Preferably, the subject is a mammal. The term "mammal", as used herein, refers to any mammalian species, including but not being limited to domestic and farm animals (cows, horses, pigs, sheep, goats, dogs, cats or rodents), primates, and humans. Preferably, the mammal is a human being.

Compounds of Formula (I)

In the first aspect, the present invention provides a compound of formula (I) for use in the treatment and/or prevention of an obesity-related condition selected from the group consisting of obesity, lipid storage disease (in particular hepatic steatosis) and hyperlipemia.

In one embodiment, the present invention provides compounds of formula (I) for use in the treatment and/or prevention of an obesity-related condition selected from the group consisting of obesity, lipid storage disease (in particular hepatic steatosis) and hyperlipemia wherein X is selected from the group consisting of a single bond, an oxygen atom and a —NH— group, when X is O, $R_1$ is selected from the group consisting of a) $C_{1-8}$-alkyl, b) $C_{6-10}$-aryl-$C_{1-4}$alkyl and c) $C_{5-10}$heteroaryl-$C_{1-4}$alkyl wherein the $C_{5-10}$heteroaryl rest comprises 1 to 3 heteroatoms selected from the group consisting of nitrogen, oxygen and sulphur, when X is an single bond or a —NH— group, $R_1$ is selected from the group consisting of d) phenyl optionally substituted by 1 to 3 substituents selected from the group consisting of OH, $NR_5R_6$, CN, $CF_3$, $C_{1-6}$ linear or branched alkyl; $C_{1-6}$ linear or branched alkoxy and halogen atoms; e) naphthyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; f) $C_{5-10}$heterocyclyl-$C_{0-2}$alkyl wherein the heterocyclyl rest is saturated or unsaturated and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g) $C_{1-6}$ linear or branched alkyl and h) $C_{3-6}$cycloalkyl-$C_{0-2}$alkyl optionally substituted by 1 to 3 substituents selected from the group consisting of OH, $NR_5R_6$, CN, $CF_3$, $C_{1-6}$ linear or branched alkyl and halogen atoms;

$R_2$ is selected from the group consisting of i) $C_{1-8}$-alkyl, j) $C_{1-8}$-alkoxy-O—$C_{1-8}$-alkyl and k) $C_{3-6}$cycloalkyl-$C_{0-2}$alkyl;

$R_3$ is selected from the group consisting of l) $C_{1-8}$-alkyl and m) benzyl optionally substituted by 1 to 3 substituents selected from the group consisting of $C_{1-4}$-alkyl, MeO, CN and halogen atoms;

$R_4$ is selected from the group consisting of n) $C_{1-8}$-alkyl and o) $C_{3-6}$cycloalkyl-$C_{0-2}$alkyl optionally substituted by $C_{1-4}$-alkyl; and $R_5$ and $R_6$ are independently selected from the group consisting of hydrogen atoms and $C_{1-6}$ linear or branched alkyl groups;

or a pharmaceutically acceptable salt thereof.

In one embodiment, the present invention provides compounds of formula (I) for use in the treatment and/or prevention of an obesity-related condition selected from the group consisting of obesity, lipid storage disease (in particular hepatic steatosis) and hyperlipemia wherein X is a single bond.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein X is selected from the group consisting of a single bond and NH and the $R_1$ group is selected from the group consisting of d) phenyl optionally substituted by 1 to 3 substituents selected from the group consisting of CN, $CF_3$, $C_{1-3}$ linear or branched alkyl; and halogen atoms and f) $C_{5-10}$heterocyclyl wherein the heterocyclyl rest is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein X is selected from the group consisting of a single bond and NH and the $R_1$ group is selected from the group consisting of d) phenyl optionally substituted by 1 to 3 substituents selected from the group consisting of CN, $CF_3$, $C_{1-3}$ linear or branched alkyl; and halogen atoms and f) a $C_{5-10}$heteroaryl selected from the group consisting of pyridinyl, pyrimidinyl and quinolinyl all of them optionally substituted by 1 to 3 substituents selected from the group consisting of OH, $NH_2$, $N(CH_3)_2$, CN, $CF_3$, $C_{1-6}$ linear or branched alkyl and halogen atoms.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia, wherein $R_1$ is selected from the group consisting of d) phenyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy (preferably methoxy) and halogen atoms; and f) $C_{5-10}$heterocyclyl-$C_{0-2}$alkyl wherein the heterocyclyl rest is saturated or unsaturated and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia, wherein $R_1$ is selected from the group consisting of d) phenyl optionally substituted by 1 to 3 $C_{1-6}$ linear or branched alkoxy substituents (preferably methoxy); and f) $C_{5-10}$heterocyclyl wherein the heterocyclyl rest is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia, wherein $R_1$ is selected from the group consisting of d) phenyl optionally substituted by 1 to 3 $C_{1-6}$ linear or branched alkoxy substituents (preferably methoxy); and f) $C_{5-10}$heterocyclyl wherein the heterocyclyl selected from the group consisting of pyridinyl, pyrimidinyl and quinolinyl, all of them optionally substituted by 1 to 3 substituents selected from the group consisting of OH, $NH_2$, $N(CH_3)_2$, CN, $CF_3$, $C_{1-6}$ linear or branched alkyl and halogen atoms.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein the $R_2$ group is selected from the group consisting of $C_{2-5}$ linear or branched alkyl and $C_{3-5}$ cycloalkyl.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein the $R_2$ group is selected from the group consisting isopropyl, propyl, and cyclopropyl, preferably isopropyl.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein the $R_3$ group is benzyl optionally substituted by 1 to 3 substituents selected from the group consisting of $C_{1-4}$-alkyl, MeO, CN and halogen atoms.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein the $R_4$ group is selected from the group consisting of $C_{2-5}$ linear or branched alkyl and $C_{3-5}$ cycloalkyl both optionally substituted by $C_{1-4}$-alkyl.

In another embodiment, the present invention provides compounds of formula (I), as defined for the first aspect of the invention, for use in the treatment and/or prevention of an obesity-related condition selected from the group consisting of obesity, lipid storage disease (in particular hepatic steatosis) and hyperlipemia wherein the $R_4$ group is selected from the group consisting of ethyl, tert-butyl and cyclopropyl.

In the second aspect, the present invention relates to the use of a compound of formula (I) as defined above, or pharmaceutically acceptable salt thereof, for the manufacture of a medicament for the treatment and/or prevention of an obesity-related condition selected from the group consisting of obesity, lipid storage disease (in particular hepatic steatosis) and hyperlipemia.

In the third aspect, the present invention relates to a method of treatment and/or prevention of an obesity-related condition selected from the group consisting of obesity, lipid storage disease (in particular hepatic steatosis) and hyperlipemia in a subject in need thereof, which comprises administering to said subject a therapeutically effective amount of a compound of formula (I) as defined above or a pharmaceutically acceptable salt thereof.

Process for the Preparation of Compounds of Formulae (I) or (II)

The compounds of formula (I) or (II) may be prepared starting from the N-substituted 3-amino-2-hydroxy-amide hydrochlorides of formula (VIII) following the synthetic scheme shown below:

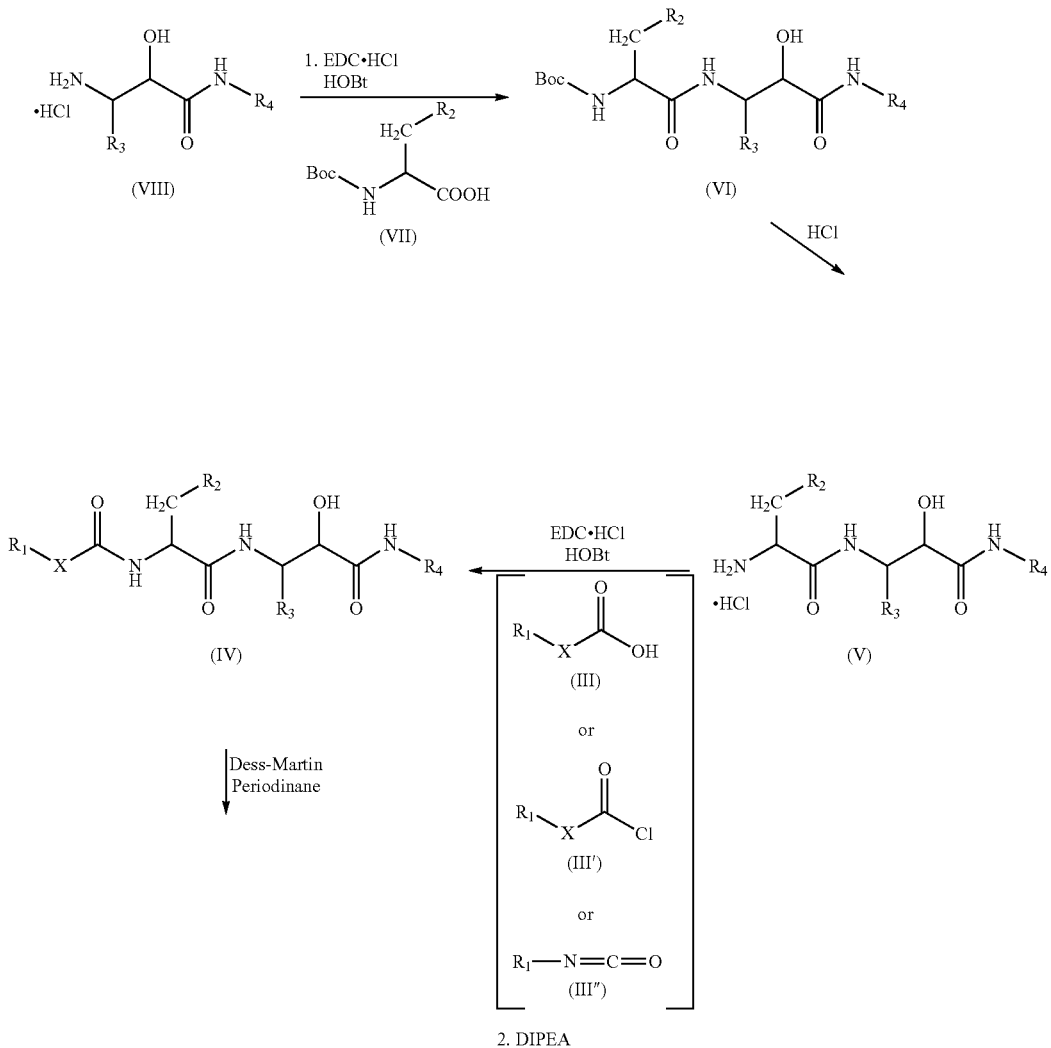

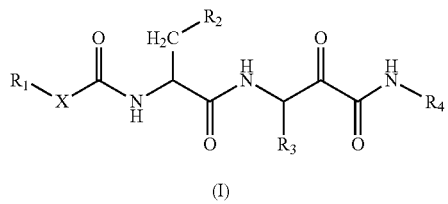

(I)

In a first step the protected aminoacid of formula (VII), HOBt (hydroxybenzotriazol), EDC-HCl (1-ethyl-3-(3-dimethylaminopropyl)carbodiimide hydrochloride) and the N-substituted 3-amino-2-hydroxy-amide hydrochlorides of formula (VIII) are dissolved in a solvent such as dichloromethane (DCM). DIPEA (N,N-diisopropylethylamine) is then added and the mixture is left to react to yield the compound of formula (VI). Other amide coupling agents are equally effective such us HATU in the presence of DIPEA in DMF or T3P in the presence of $NEt_3$ in DMF.

The compound of formula (VI) was reacted in a solvent such as 1,4-dioxane with a strong acid such as hydrochloric acid or in DCM and treated with TFA to yield the compound of formula (V).

When X is a bond, the compound of formula (III, HOBt (hydroxybenzotriazol), EDC-HCl (1-ethyl-3-(3-dimethylaminopropyl)carbodiimide hydrochloride) and the compound of formula (V) are dissolved in a solvent such as DCM. DIPEA (N,N-diisopropylethylamine) is then added and the mixture is left to react to yield the compound of formula (IV). Other amide coupling agents are equally effective such as HATU in the presence of DIPEA in DMF or T3P in the presence of $NEt_3$ in DMF.

When X is O, the compound of formula (IV) can be prepared starting from compound (V) by reaction with a carbono hydrochloride derivative (III') in an aprotic solvent such as DCM or by reaction with carbonyl imidazol and the corresponding alcohol.

When X is NH, the compound of formula (IV) can be prepared starting from compound (V) by reaction with a isocyanate derivative (III") in an aprotic solvent such as DCM or toluene.

Finally, the compound of formula (IV) is dissolved in solvents such as DCM, DMF or a mixture of them and Dess-Martin periodinane is added to yield the compound of formula (I). Other oxidants such as DCC in DMSO are equally useful.

The N-substituted 3-amino-2-hydroxy-amide hydrochlorides of formula (VIII) may be obtained starting from the protected aminoaldehydes of formula (XIII) following the synthetic scheme shown below:

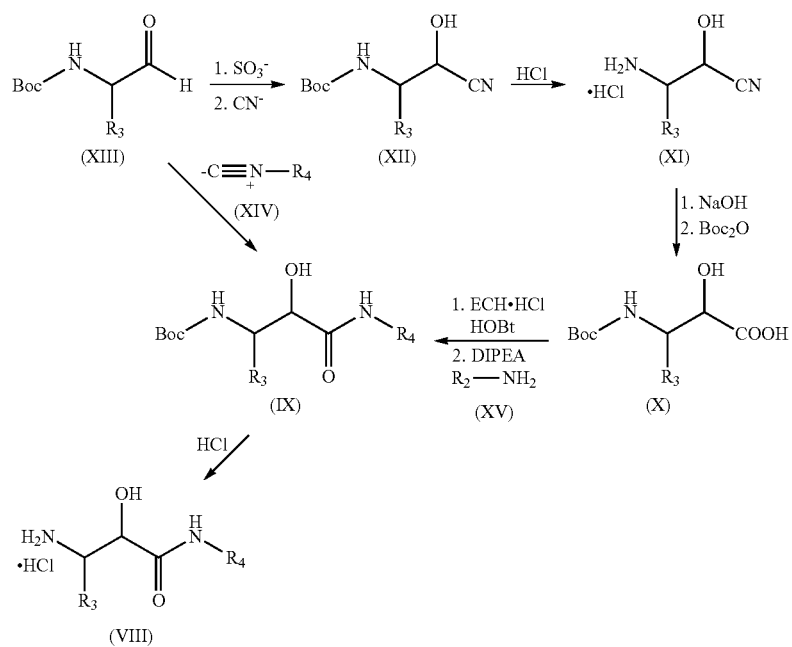

In a first step the protected aminoaldehydes of formula (XIII) are dissolved in a solvent such as 1,4-dioxane and sodium bisulfite is added followed by the addition of a potassium cyanide aqueous solution to yield the compound of formula (XII).

The compound of formula (XII) is dissolved in a concentrated acid aqueous solution such as concentrated hydrochloric acid and refluxed to yield the compound of formula (XI).

An aqueous solution of compound of formula (XI) is brought to alkaline pH (preferably in the range of 10-12) for example with sodium hydroxide and $Boc_2O$ (di-tert-butyl dicarbonate) is added. After total conversion the mixture is acidified for example with KHSO₄ and the compound of formula (X) is extracted with a water-immiscible solvent such as ethyl acetate.

The compound of formula (X), HOBt (hydroxybenzotriazol), EDC·HCl (1-ethyl-3-(3-dimethylaminopropyl)carbodiimide hydrochloride) are dissolved in a solvent such as anhydrous DCM. DIPEA (N,N-diisopropylethylamine) and the amine of formula (XV) are then added and the mixture is left to react for 8 to 24 hours react to yield the compound of formula (VIII). T3P or HATU can also be used instead of EDC.HCl and HOBt with good results).

The compound of formula (IX) was reacted in a solvent such as 1,4-dioxane with a strong acid such as hydrochloric acid to yield the compound of formula (V).

In an alternative synthetic path which is also illustrated in the previous scheme, the protected aminoaldehydes of formula (XIII) are dissolved in a solvent such as anhydrous DCM and an acid such as acetic acid and an isocyanide compound of formula (XIV) are added and left to react in an inert atmosphere such as Argon atmosphere at room temperature. Then solvent is removed and the resulting compound is extracted with ethyl acetate and washed with a saturated sodium bicarbonate aqueous solution. The product was then solved in a mixture of THF (tetrahydrofurane) and MeOH (methanol) and treated with a lithium hydroxide aqueous solution to yield the compound of formula (IX).

Then, the compound of formula (IX) is reacted, as described above, in a solvent such as 1,4-dioxane with a strong acid such as hydrochloric acid to yield the compound of formula (VIII).

The starting compounds of formulae (XIII), (XIV), (XV), (VII) and (III) are either commercially available or may be obtained by methods described in the literature.

Thus, in a further aspect, the present invention relates to a process for the preparation of a compound of formula (II) as defined herein, which comprises the reaction of a compound of formula (IV) with Dess-Martin periodinane

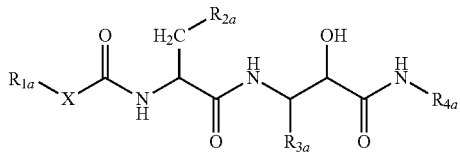

(IV)

wherein X, $R_{1a}$, $R_{2a}$, $R_{3a}$ and $R_{4a}$ are as defined for the compounds of formula (II).

Use of Compounds of Formula (I) or (II)
Non-Therapeutic Use

The dipeptidyl ketoamide compounds of formulae (I) or (II) as defined above are capable of reducing adipogenesis and/or the deposition of increased amounts of cytoplasmic triglyceride or lipid droplets in adipocytes, thereby being capable to prevent accumulation of triglycerides in adipose tissue and/or to reduce the amount of triglycerides in adipose tissue. This property allows the non-therapeutic use of a compound of formula (I) or formula (II).

In particular, one aspect of the invention relates to the non-therapeutic use of a compound of formula (I) as previously defined in the first aspect of the invention to reduce fat accumulation, for example to improve bodily appearance, in a subject which does not suffer from obesity or other obesity-related pathological conditions, such as lipid storage disease (in particular hepatic steatosis) and hyperlipemia.

Therapeutic Use

The capacity of the dipeptidyl ketoamide compounds of formula (I) or (II) as defined to reduce adipogenesis and/or the deposition of increased amounts of cytoplasmic triglyceride or lipid droplets in adipocytes also allows the therapeutic use of said compounds to in the treatment and/or prevention an obesity-related condition selected from the group consisting of obesity, lipid storage disease (in particular hepatic steatosis) and hyperlipemia by administration of said compounds to a subject in need thereof, particularly to a subject suffering from obesity or at risk of suffering obesity.

Compounds of Formula (II)

In the fifth aspect, the present invention provides a compound of formula (II) as previously defined. Compounds of formula (II) are a subgroup of compounds of formula (I) which have not been previously disclosed.

In one embodiment the present invention provides compounds of formula (II), as defined for the fifth aspect of the invention, wherein X is selected from the group consisting of a single bond, an oxygen atom and a —NH— group, when X is O, $R_{1a}$ is selected from the group consisting of a1) $C_{1-8}$-alkyl, b1) $C_{6-10}$-aryl-$C_{1-4}$alkyl and c1) $C_{5-10}$heteroaryl-$C_{1-4}$alkyl wherein the $C_{5-10}$heteroaryl rest comprises 1 to 3 heteroatoms selected from the group consisting of nitrogen, oxygen and sulphur, when X is an single bond, $R_{1a}$ is selected from the group consisting of d1) phenyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; f1) $C_{5-10}$heterocyclyl-$C_{0-2}$alkyl wherein the heterocyclyl rest comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g1) $C_{1-6}$ linear or branched alkyl and h1) $C_{3-6}$cycloalkyl-$C_{0-2}$alkyl optionally substituted by 1 to 3 substituents selected from the group consisting of OH, $NR_{5a}R_{6a}$, CN, $CF_3$, $C_{1-6}$ linear or branched alkyl and halogen atoms;

when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NR_{5a}R_{6a}$, CN, $CF_3$, $C_{1-6}$ linear or branched alkyl and halogen atoms; f2) $C_{5-10}$heterocyclyl-$C_{0-2}$alkyl wherein the heterocyclyl rest comprises 1 to 3 heteroatoms selected from the group consisting of nitrogen, oxygen and sulphur and is optionally substituted by 1 to 3 substituents selected from the group consisting of OH, $NR_{5a}R_{6a}$, CN, $CF_3$, $C_{1-6}$ linear or branched alkyl and halogen atoms; g2) $C_{1-6}$ linear or branched alkyl and h2) $C_{3-6}$cycloalkyl-$C_{0-2}$alkyl optionally substituted by 1 to 3 substituents selected from the group consisting of OH, $NH_2$, CN, $CF_3$, $C_{1-6}$ linear or branched alkyl and halogen atoms;

$R_{2a}$ is selected from the group consisting of i1) $C_{1-8}$-alkyl, j1) $C_{1-8}$-alkoxy-$C_{1-8}$-alkyl and k1) $C_{3-6}$cycloalkyl-$C_{0-2}$alkyl with the proviso that when X is O then $R_{2a}$ is not an isopropyl group, $R_{3a}$ is selected from the group consisting of l1) $C_{1-8}$-alkyl and m1) benzyl optionally substituted by 1 to 3 substituents selected from the group consisting of $C_{1-4}$-alkyl, MeO, CN and halogen atoms with the proviso that when X is a single bond and $R_{1a}$ is a $C_{5-10}$heterocyclyl-$C_{0-2}$alkyl group, $R_{3a}$ is not an ethyl group;

$R_{4a}$ is selected from the group consisting of n1) $C_{1-8}$-alkyl and o1) $C_{3-6}$cycloalkyl-$C_{0-2}$alkyl optionally substituted by $C_{1-4}$-alkyl; and $R_{5a}$ and $R_{6a}$ are independently selected from the group consisting of hydrogen atoms and $C_{1-6}$ linear or branched alkyl groups;

or a pharmaceutically acceptable salt thereof.

In one embodiment the present invention provides compounds of formula (II), as defined for the fifth aspect of the invention, wherein X is a single bond.

In another embodiment the present invention provides compounds of formula (II), as defined for the fifth aspect of the invention, wherein either i) X is selected from the group consisting of O and NH and the $R_{1a}$ group is selected from the group consisting of a1) $C_{1-6}$-alkyl or ii) X is a single bond and the $R_{1a}$ group is selected from the group consisting of d1) phenyl optionally substituted by 1 to 3 substituents selected from the group consisting of CN, $CF_3$, $C_{1-3}$ linear or branched alkyl, $C_{1-3}$ linear or branched alkoxy (preferably methoxy) and halogen atoms and f1) $C_{5-10}$heterocyclyl wherein the heterocyclyl rest is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen.

In another embodiment the present invention provides compounds of formula (II), as defined for the fifth aspect of the invention, wherein X is a single bond and the $R_{1a}$ group is selected from the group consisting of d1) phenyl optionally substituted by 1 to 3 $C_{1-3}$ linear or branched alkoxy (preferably methoxy), and f1) $C_{5-10}$heterocyclyl wherein the heterocyclyl rest is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen.

In another embodiment the present invention provides compounds of formula (II), as defined for the fifth aspect of the invention, wherein either i) X is selected from the group consisting of O and NH and the $R_{1a}$ group is selected from the group consisting of a1) $C_{1-6}$-alkyl or ii) X is a single bond and the $R_{1a}$ group is selected from the group consisting of d1) phenyl optionally substituted by 1 to 3 substituents selected from the group consisting of CN, $CF_3$, $C_{1-3}$ linear or branched alkyl, and halogen atoms and f1) $C_{5-10}$heterocyclyl wherein the heterocyclyl rest is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen.

In another embodiment the present invention provides compounds of formula (II), as defined for the fifth aspect of the invention, wherein either i) X is selected from the group consisting of O and NH and the $R_{1a}$ group is selected from the group consisting of a1) $C_{1-8}$-alkyl or ii) X is an single bond and the $R_{1a}$ group is selected from the group consisting of d1) phenyl optionally substituted by 1 to 3 substituents selected from the group consisting of CN, $CF_3$, $C_{1-3}$ linear or branched alkyl, and halogen atoms and f1) a $C_{5-10}$heterocyclyl wherein the heterocyclyl rest is heteroaromatic and is selected from the group consisting of pyridinyl, pyrimidinyl and optionally substituted by 1 to 3 substituents selected from the group consisting of OH, $NH_2$, $N(CH_3)_2$, CN, $CF_3$, $C_{1-6}$ linear or branched alkyl and halogen.

In another embodiment the present invention provides compounds of formula (II), as defined for the fifth aspect of the invention, wherein either X is an single bond and the $R_{1a}$ group is selected from the group consisting of d1) phenyl optionally substituted by 1 to 3 $C_{1-3}$ linear or branched alkoxy (preferably methoxy) substituents and f1) a $C_{5-10}$heterocyclyl wherein the heterocyclyl rest is heteroaromatic and is selected from the group consisting of pyridinyl, pyrimidinyl and optionally substituted by 1 to 3 substituents selected from the group consisting of OH, $NH_2$, $N(CH_3)_2$, CN, $CF_3$, $C_{1-6}$ linear or branched alkyl and halogen.

In another embodiment the present invention provides compounds of formula (II), as defined for the fifth aspect of the invention, wherein either i) X is selected from the group consisting of O and NH and the $R_{1a}$ group is selected from the group consisting of a1) $C_{1-8}$-alkyl or ii) X is an single bond and the $R_{1a}$ group is selected from the group consisting of d1) phenyl optionally substituted by 1 to 3 substituents selected from the group consisting of CN, $CF_3$, $C_{1-3}$ linear or branched alkyl; and halogen atoms and f1) a $C_{5-10}$heterocyclyl wherein the heterocyclyl rest is heteroaromatic and is selected from the group consisting of pyridinyl, pyrimidinyl and optionally substituted by 1 to 3 substituents selected from the group consisting of OH, $NH_2$, $N(CH_3)_2$, CN, $CF_3$, $C_{1-6}$ linear or branched alkyl and halogen.

In another embodiment the present invention provides compounds of formula (II), as defined for the third aspect of the invention, wherein X is a single bond.

In another embodiment the present invention provides compounds of formula (II), as defined for the third aspect of the invention, wherein the $R_{2a}$ group is selected from the group consisting of $C_{2-5}$ linear or branched alkyl and $C_{3-5}$ cycloalkyl with the proviso that when X is O then $R_{2a}$ is not an isopropyl group.

In another embodiment the present invention provides compounds of formula (II), as defined for the third aspect of the invention, wherein the $R_{2a}$ group is selected from the group consisting of isopropyl, propyl and cyclopropyl, preferably isopropyl, with the proviso that when X is O then $R_{2a}$ is not an isopropyl group.

In another embodiment the present invention provides compounds of formula (II), as defined for the third aspect of the invention, wherein the $R_{3a}$ group is benzyl optionally substituted by 1 to 3 substituents selected from the group consisting of $C_{1-4}$-alkyl, MeO, CN and halogen atoms.

In another embodiment the present invention provides compounds of formula (II), as defined for the third aspect of the invention, wherein the $R_{4a}$ group is selected from the group consisting of $C_{2-5}$ linear or branched alkyl and $C_{3-5}$ cycloalkyl both optionally substituted by $C_{1-4}$-alkyl.

In another embodiment the present invention provides compounds of formula (II), as defined for the third aspect of the invention, wherein the $R_{4a}$ group is selected from the group consisting of ethyl, tert-butyl and cyclopropyl.

Pharmaceutical Compositions/Formulations and Administration

In another aspect, the present invention provides a pharmaceutical composition comprising a compound of formula (II) as defined above, or a stereoisomer or pharmaceutically acceptable salt thereof, and one or more pharmaceutically acceptable excipients.

The term "pharmaceutically acceptable excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005.

Compounds of formula (II) of the invention may be administered by the oral, sublingual, parenteral, subcutaneous, intramuscular, intravenous, transdermal, intranasal, intraocular, and/or rectal routes. The compounds may be administered alone or in combination with one or more other compounds of the invention or one or more other drugs.

The pharmaceutical compositions of the present invention may comprise the compounds of formula (II) within liposomes or microvesicles, and may be in the form of dispersions, solutions, lotions, gels, and the like, including topical preparations.

EXAMPLES

Abbreviations

The following abbreviations are used in the examples:
ACN: acetonitrile
Boc: tert-butoxycarbonyl
conc: concentrate
$Boc_2O$: di-tert-butyl dicarbonate
DCC: N,N'-Dicyclohexylcarbodiimide
DCM: dichloromethane
DIPEA: N,N-Diisopropylethylamine
DMEM: Dulbecco/Vogt modified Eagle's minimal essential medium
DMF: Dimethylformamide
DMSO: dimethylsulfoxide
EDC HCl: 1-ethyl-3-(3-dimethylaminopropyl)carbodiimide hydrochloride
EtOAc: ethyl acetate
EtOH: ethanol
FBS: Fetal bovine serum
HEPES: 4-(2-hydroxyethyl)-1-piperazineethanesulfonic acid
HATU: 1-[Bis(dimethylamino)methylene]-1H-1,2,3-triazolo[4,5-b]pyridinium 3-oxid hexafluorophosphate
HOBt: hydroxybenzotriazol
MeOH: methanol
Min: minutes
$NEt_3$: Triethylamine
T3P: n-propyl phosphonic acid cyclic anhydride
TEA: triethylamine
TFA: Trifluoroacetic acid
THF: tetrahydrofuran
Tris-HCl: tris(hydroxymethyl) aminomethane hydrochloride
tR: retention time
LC-MS: liquid chromatography-mass spectrometry
Leu-OH: Leucine
Sat: saturated
HCl: Hydrochloric Acid
HBTU: N,N,N',N'-Tetramethyl-O-(1H-benzotriazol-1-yl)uronium hexafluorophosphate
HSe: Homoserine
DCHA: Dicyclohexylamonium Materials and Methods The products of the examples were characterised using liquid chromatography coupled to mass spectroscopy (LC-MS).

HPLC-MS analysis was carried out using one of the three following procedures:
Method A:
In an Alliance HT 2795 (Waters) chromatograph equipped with 2996 photodiode array detector and coupled to micromass ZQ4000 detector LC/MS. Separation was achieved using a YMC-Pack ODS-AQ column (50×4.6 mm, S-3 μm) and using mixtures of a 0.1% formic acid aqueous solution (A) a 0.1% solution of formic acid in acetonitrile (B) as eluents at 50° C. and 1.6 mL/min flow rate using the following eluting conditions: 5% to 100% B in 3.5 min. The detector was set at electrospray positive mode (ESI+) in the mass range of 100-700. Cone voltage 10 V. Source T: 120° C. Desolvation T: 350° C.
Method B:
In a an Alliance HT 2795 (Waters) chromatograph equipped with 2996 photodiode array detector and coupled to mass 3100 detector LC/MS. Separation was achieved using a XBridge C18 column (50×4.6 mm, S-3.5 μm) and using mixtures of a 10 mM $NH_4CO_3$ aqueous solution of pH=9 (A) and acetonitrile (B) as eluents at 50° C. and 1.6 mL/min flow rate using the following eluting conditions: 5% to 100% B in 3.5 min. The detector was set at electrospray positive mode (ESI+) in the mass range of 100-700. Cone voltage 10 V. Source T: 120° C. Desolvation T: 350° C.
Method C:
In a AcQuity Ultraperformance LC chromatograph equipped with PDA detector and coupled to MS (SQD#M06SQD003W), separation was achieved using a ACQUITY UPLC BEH C18 column (50×2.1 mm, 1.7 μm) and using mixtures of a 10 mM $NH_4HCO_3$ aqueous solution (B) and acetonitrile (A) as eluents at 40° C. and 0.5 mL/min flow rate using the following eluting conditions: 10% to 90% A in 3.0 min. The PDA detector was set at 190-400 nm (samples were read at 220 and 260 nm).

Reference Example 1: Synthesis of (3S)-3-amino-N-ethyl-2-hydroxy-4-phenylbutanamide (vi)

Step-1: tert-butyl ((2S)-1-cyano-1-hydroxy-3-phenylpropan-2-yl)carbamate (ii)

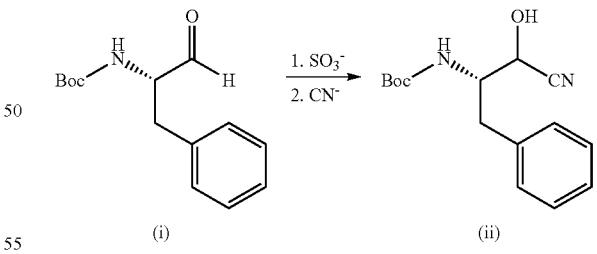

(i)            (ii)

To a solution of (S)-tert-butyl 1-oxo-3-phenylpropan-2-ylcarbamate (i) (1.49 g, 5.98 mmol) in 1,4-dioxane (5 mL) at 0° C., was added sodium bisulfate (4 eq). Reaction mixture was stirred at 0° C. for 10 minutes and potassium cyanide (4 eq) was added dissolved in water (1 mL). Reaction mixture was stirred for 2 hours.

Water and EtOAc were added, layers were separated. Combined organic layers were washed with sat. aq. $NaHCO_3$, dried and concentrated under reduced pressure. (1.2 g, 99%)

LC-MS (Method A): tR=2.73 min; m/z=277 (MH$^+$).

Step-2: (3S)-3-amino-2-hydroxy-4-phenylbutanoic acid hydrochloride (iii)

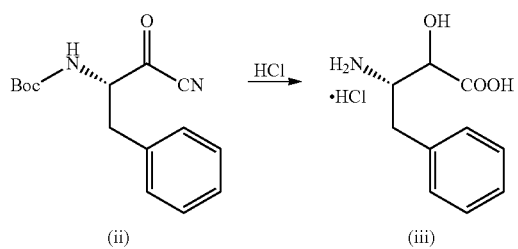 [SMILES: CC(C)(C)OC(=O)N[C@@H](Cc1ccccc1)C(=O)C#N ; Cl ; Cl ; N[C@@H](Cc1ccccc1)C(O)C(=O)O]

Compound (ii) obtained in step-1, was dissolved in 10 ml of Conc. HCl solution and refluxed for 2 hours. Then, the solution was cooled and neutralized with NaOH 3 N until pH 11. Extracted with EtOAc.

The aqueous layer was used with next step without further purification (quantitative yield)

LC-MS (Method B): tR=0.88-1.00 min; m/z=196 (MH$^+$).

Step-3: (3S)-3-((tert-butoxycarbonyl)amino)-2-hydroxy-4-phenylbutanoic Acid (iv)

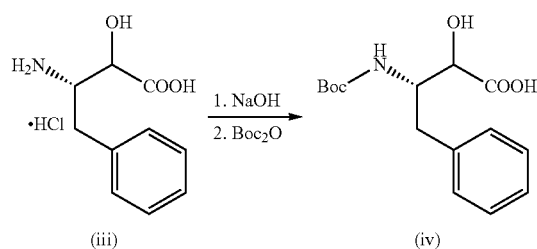 [SMILES: Cl ; N[C@@H](Cc1ccccc1)C(O)C(=O)O ; CC(C)(C)OC(=O)N[C@@H](Cc1ccccc1)C(O)C(=O)O]

To the aqueous layer resulting from step-2 comprising compound (iii) 40 ml of 3 M NaOH were added until pH was 11 and then, 4.2 g Boc2O were added. The mixture was stirred at room temperature for 2 hours. After total conversion was achieved mixture was acidified with KHSO$_4$ to pH 2 and extracted with EtOAc. The organic layer was evaporated and the resulting product was used for next step without further purification. (0.44 g, 32% 2 steps)

LC-MS (Method B): tR=1.68 min; m/z=296 (MH+).

Step-4: tert-butyl ((2S)-4-(ethylamino)-3-hydroxy-4-oxo-1-phenylbutan-2-yl)carbamate (v)

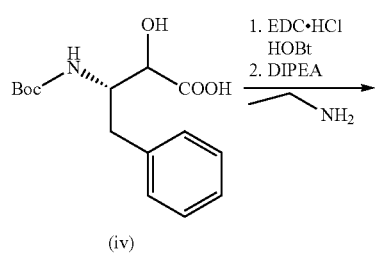

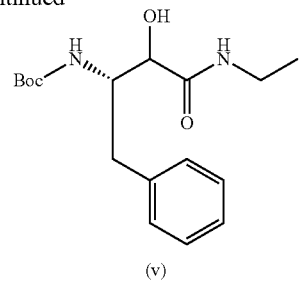

(4 mL) of EDC.HCl (1.15 eq) and of HOBt (1.15 eq) were added to a stirred solution of the product (iv) of step 3 (440 mg, 1.475 mmol) in anhydrous DCM. After 15 min, DIPEA (4 eq) and ethylamine (2M, THF solution, 6 eq) were added and the resulting mixture was stirred at room temperature.

After 16 h, T3P (2 eq) and DIPEA (2 more eq) were added. After 4 h there was a slight improvement in conversion. It was allowed to stir at room temperature.

Volatiles were removed under vacuum and crude extracted with EtOAc washed with a sat. Solution of NaHCO$_3$ (2×20 mL).

Crude was purified on ISCO Rf using Hexanes/Hexanes: EtOH (8:2) as solvents, from 0 to 10% in B, product eluted at 10% in B). 130 mg were obtained. (130 mg, 27% yield)

LC-MS (Method B): tR=2.3 min; m/z=323 (MH$^+$).

Step-5: (3S)-3-amino-N-ethyl-2-hydroxy-4-phenylbutanamide hydrochloride (vi)

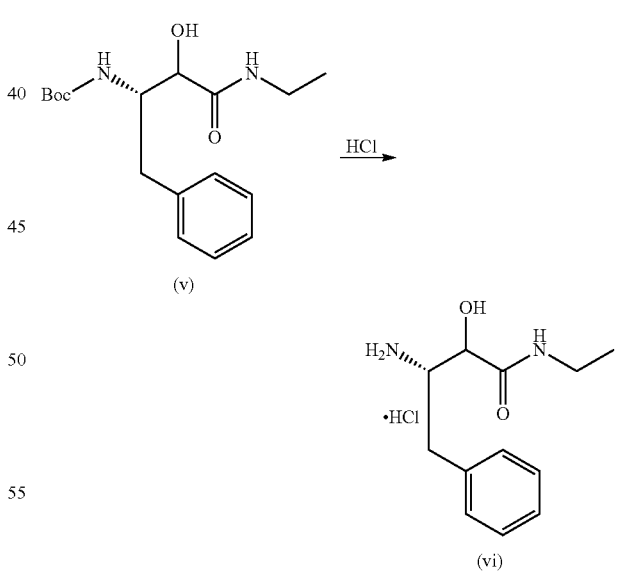

HCl 4 N in 1,4-dioxane was added to tert-butyl (2S)-4-(ethylamino)-3-hydroxy-4-oxo-1-phenylbutan-2-ylcarbamate (v) (0.83 g, 2.57 mmol) and the mixture was stirred at room temperature for 3 h. The crude was concentrated and the resulting product was used for next step without further purification (quantitative yield).

LC-MS (Method C): tR=1.07 min; m/z=223 (MH$^+$).

Reference Example 2: (2S)-2-amino-N-(4-(ethylamino)-3-hydroxy-4-oxo-1-phenylbutan-2-yl)-4-methylpentanamide hydrochloride (ix)

Step-1: tert-butyl ((2S)-1-((4-(ethylamino)-3-hydroxy-4-oxo-1-phenylbutan-2-yl)amino)-4-methyl-1-oxopentan-2-yl)carbamate (viii)

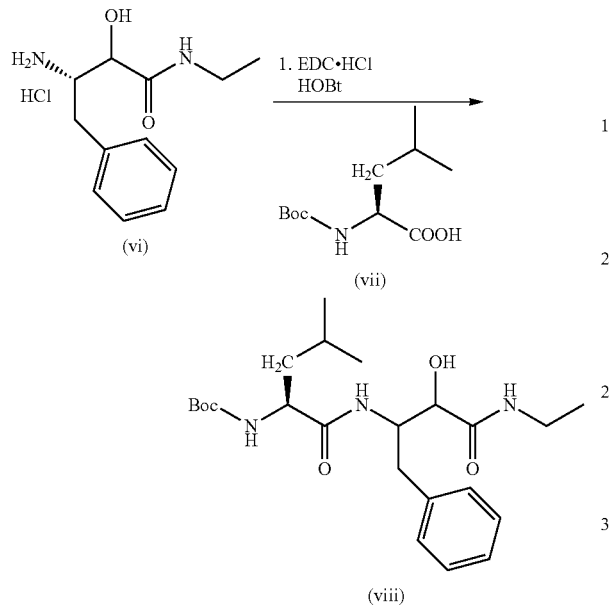

(2S)-tert-Butoxycarbonylamino-4-methyl-pentanoic acid (vii) (964 mg, 1.3 eq), EDC.HCl (856 mg, 1.5 eq), HOBt (684 mg, 1.5 eq) and the compound (vi) of reference example 1 (770 mg, 2.98 mmol) were dissolved in DCM (10 ml) then, DIPEA (2 ml 4 eq) was added. The mixture was stirred for 16 h at room temperature. The solvent was evaporated. The resulting residue was dissolved in EtOAc and washed with a saturated NH₄Cl solution and a saturated NaHCO₃ solution. The combined organic layers were evaporated under reduced pressure. The product (viii) was purified through column chromatography on ISCO Rf using DCM and MeOH as solvents. (1.35 g, quantitative yield)

LC-MS (Method B): tR=2.6 min; m/z=436 (MH⁺).

Step-2: (2S)-2-amino-N-(4-(ethylamino)-3-hydroxy-4-oxo-1-phenylbutan-2-yl)-4-methylpentanamide hydrochloride (ix)

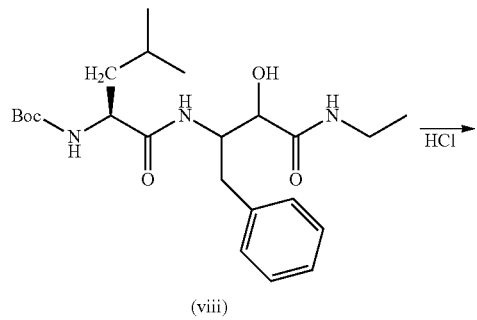

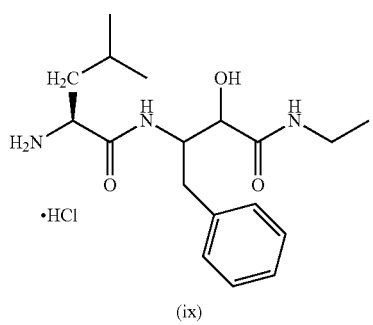

HCl 4 N in 1,4-Dioxane was added to ((2S)-1-((4-(ethylamino)-3-hydroxy-4-oxo-1-phenylbutan-2-yl)amino)-4-methyl-1-oxopentan-2-yl)carbamate (viii) and the mixture was stirred at room temperature for 3 h. The crude was concentrated and the resulting product was used for next step without further purification (quantitative yield).

LC-MS (Method B): tR=1.9-2.02 min; m/z=336 (MH⁺).

Reference Example 3: (3S)-3-amino-2-hydroxy-N-tert-pentyl-4-phenylbutanamide hydrochloride (xli)

Step-1: tert-butyl ((2S)-3-hydroxy-4-oxo-4-(tert-pentylamino)-1-phenylbutan-2-yl)carbamate (x)

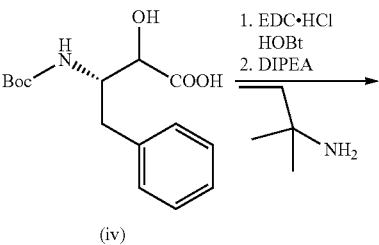

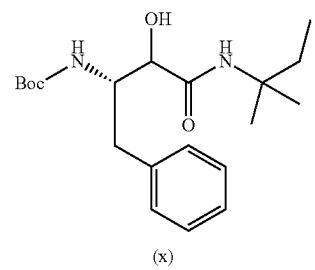

Title compound was obtained following a similar procedure to that described for product (v) in step 4 of reference example 1 but using tert-amylamine instead of ethylamine as starting material (70 mg, 11% yield).

LC-MS (Method A): tR=3.12 min; m/z=365 (MH⁺)

Step-2: (3 S)-3-amino-2-hydroxy-N-tert-pentyl-4-phenylbutanamide hydrochloride (xli)

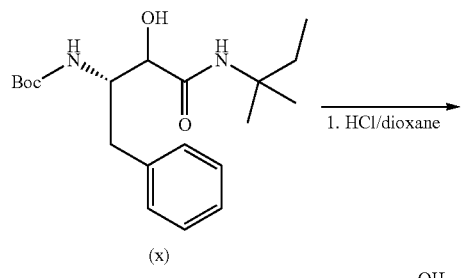

Preparation took place in a manner analogous to that described for product (vi) in step 5 of reference example 1 using compound (x) as the starting material (105 mg, quantitative yield).

LC-MS (Method A): tR=1.70-1.78 min; m/z=265 (MH$^+$)

Reference Example 4: (3S)-3-amino-N-(tert-butyl)-2-hydroxy-4-phenylbutanamide hydrochloride (xiii)

Step-1: tert-butyl ((2S)-4-(tert-butylamino)-3-hydroxy-4-oxo-1-phenylbutan-2-yl)carbamate (xii)

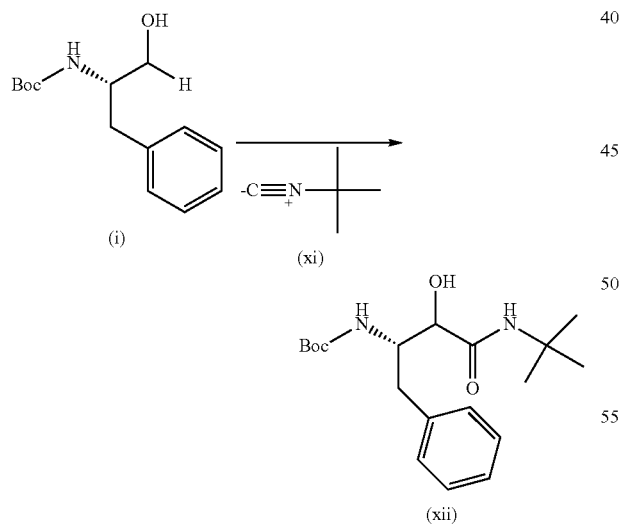

Acetic acid (1.4 ml, 2 eq) and tert-butyl isocyanide (xi) (1.5 ml, 1.1 eq) were added to a solution of (S)-tert-butyl 1-oxo-3-phenylpropan-2-ylcarbamate (i) (3.0 g, 1 eq) in anhydrous DCM (50 mL) and the mixture stirred under Argon atmosphere at room temperature.

After 1.5 h, solvent was removed under vacuum and it was extracted with EtOAc washing with NaHCO$_3$ aqueous saturated solution. It was then solved in THF:MeOH (8:3) and treated with 1M LiOH solution (1.0 g, 2 eq). After 30 min, solvents were dried under vacuum, product extracted in EtOAc washing with NaHCO$_3$ aqueous saturated solution and purified through column chromatography: ISCO (12 g, Hexanes/EtOH, from 4 to 5% in EtOH. Product eluted at 5% in EtOH. 2.48 g were obtained (59% yield).

LC-MS (Method B): tR=2.70 min; m/z=351 (MH$^+$).

Step-2: (3S)-3-amino-N-(tert-butyl)-2-hydroxy-4-phenylbutanamide hydrochloride (x)

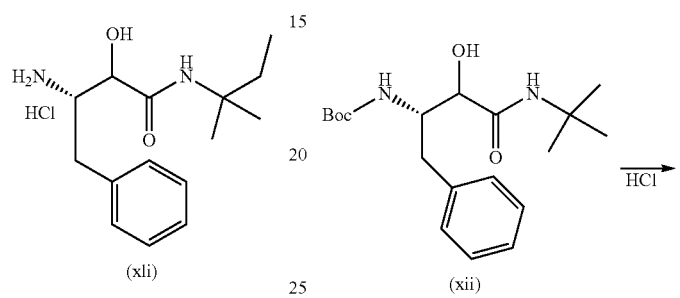

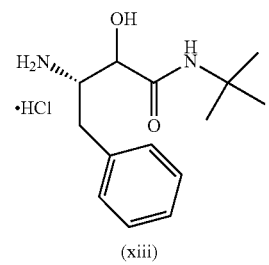

Preparation took place in a manner analogous to that described for product (vi) in step 5 of reference example 1 using compound (xii) as the starting material (3.5 g, quantitative yield).

LC-MS (Method B): tR=1.97 min; m/z=251 (MH$^+$).

Reference Example 5: 3-amino-N-cyclopropyl-2-hydroxy-4-phenylbutanamide hydrochloride (xvi)

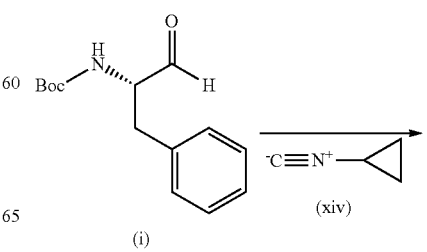

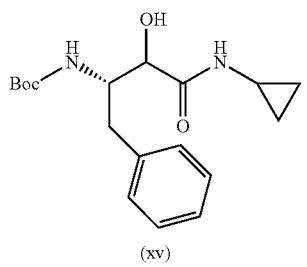

(xv)

↓ HCl

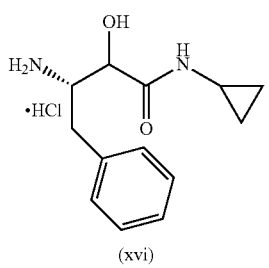

(xvi)

Title compound was obtained following a similar procedure to that described in reference example 4 but using cyclopropyl isocyanide (xiv) as starting material (631 mg, quantitative yield).

LC-MS (Method B): tR=1.55-1.62 min; m/z=235 (MH$^+$).

Reference Example 6:
3-amino-N-cyclohexyl-2-hydroxy-4-phenylbutanamide hydrochloride (xix)

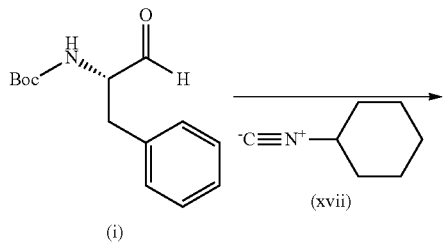

↓ HCl

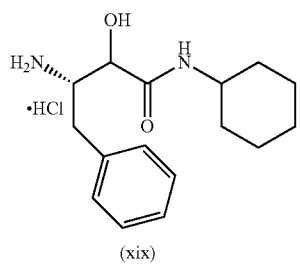

(xix)

Title compound was obtained following a similar procedure to that described in reference example 4 but using cyclohexyl isocyanide (xvii) as starting material (80 mg, quantitative yield).

LC-MS (Method B): tR=1.63 min; m/z=277 (MH$^+$).

Reference Example 7:
3-amino-N-benzyl-2-hydroxy-4-phenylbutanamide hydrochloride (xxii)

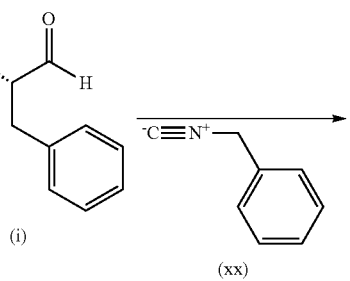

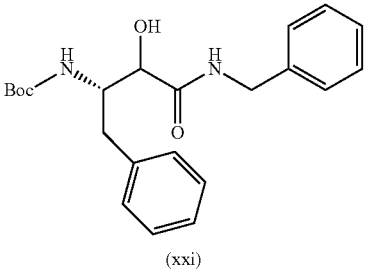

(xxi)

↓ HCl

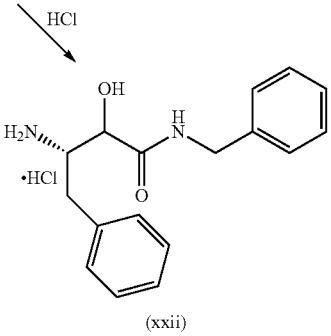

(xxii)

Title compound was obtained following a similar procedure to that described in reference example 4 but using benzyl isocyanide (xx) as starting material (100 mg, quantitative yield).

LC-MS (Method B): tR=1.62 min; m/z=285 (MH$^+$).

Reference Example 8: (2S)-2-amino-N-(4-(tert-butylamino)-3-hydroxy-4-oxo-1-phenylbutan-2-yl)-4-methylpentanamide hydrochloride (xxiv)

Step-1: tert-butyl (2S)-1-(4-(tert-butylamino)-3-hydroxy-4-oxo-1-phenylbutan-2-ylamino)-4-methyl-1-oxopentan-2-ylcarbamate (xxiii)

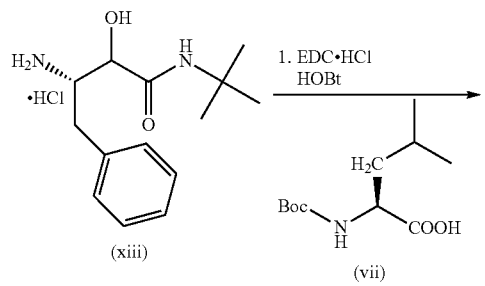

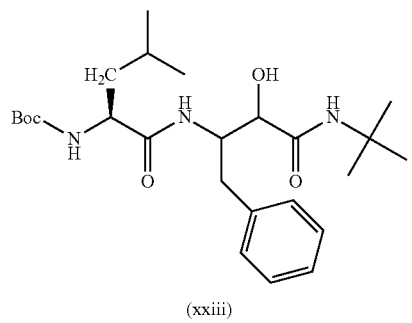

Coupling of the above described compound (xiii) (2.03 g) with (2S)-tert-butoxycarbonylamino-4-methyl-pentanoic acid (vii) (2.13 g) in a manner analogous to Reference Example 2 step 1 afforded 2.97 g (91% yield).

LC-MS (Method B): tR=2.90 min; m/z=464 (MH$^+$).

Step-2: (2S)-2-amino-N-(4-(tert-butylamino)-3-hydroxy-4-oxo-1-phenylbutan-2-yl)-4-methylpentanamide hydrochloride (xxiv)

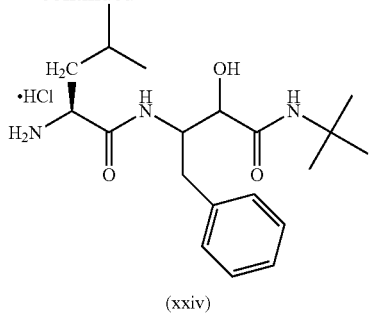

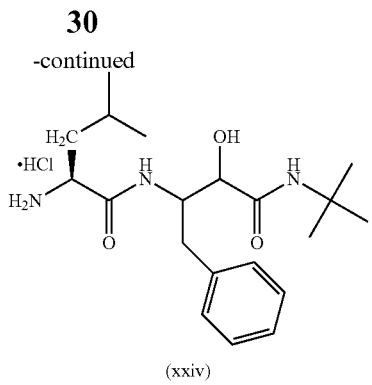

Preparation took place in a manner analogous to Reference Example 1 step 5 using compound (xxiii) as the starting material. 2.82 g were obtained (quantitative yield, 86% assumed purity) which were used for next step without further purification.

LC-MS (Method B): tR=2.28-2.40 min; m/z=364 (MH$^+$).

Reference Example 9: (2S)-2-amino-N-(4-(cyclopropylamino)-3-hydroxy-4-oxo-1-phenylbutan-2-yl)-4-methylpentanamide hydrochloride (xxvi)

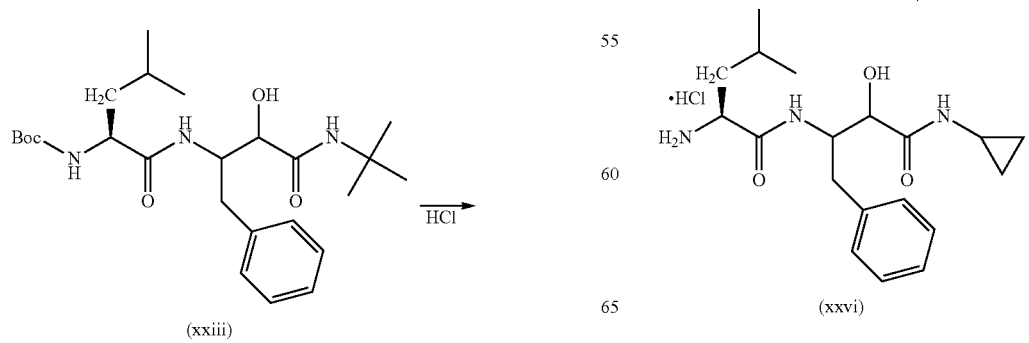

Title compound was obtained following a similar procedure to that described in reference example 8 but using compound (xvi) as the starting material. (184 mg, 44% yield)

LC-MS (Method B): tR=1.93-2.03 min; m/z=348 (MH+).

Reference Example 10: 3-((S)-2-amino-3-cyclopropylpropanamido)-N-(tert-butyl)-2-hydroxy-4-phenylbutanamide hydrochloride (xxviii)

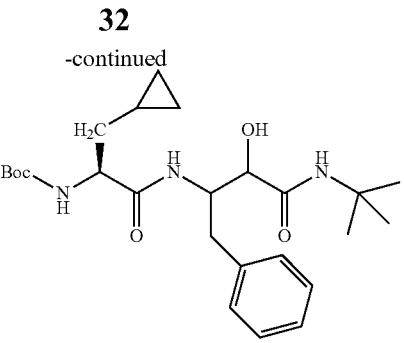

(xxvii)

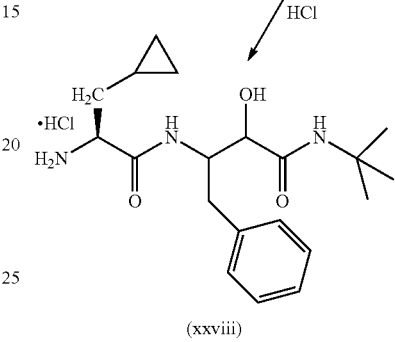

(xxviii)

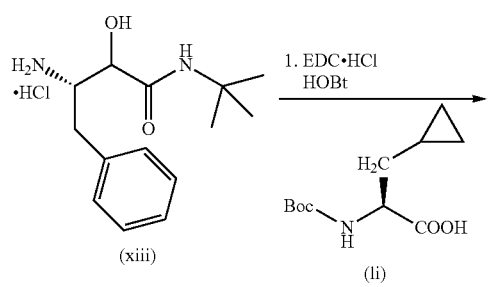

Title compound was obtained following a similar procedure to that described in reference example 8 but using compound (xiii) and (S)-2-((tert-butoxycarbonyl)amino)-3-cyclopropylpropanoic acid (li) as the starting materials (130 mg, quantitative yield)

LC-MS (Method B): tR=1.7-1.79 min; m/z=362 (MH+).

Reference Example 11: (S)-3-((S)-2-amino-4-methoxybutanamido)-N-(tert-butyl)-2-oxo-4-phenylbutanamide hydrochloride (xxxi)

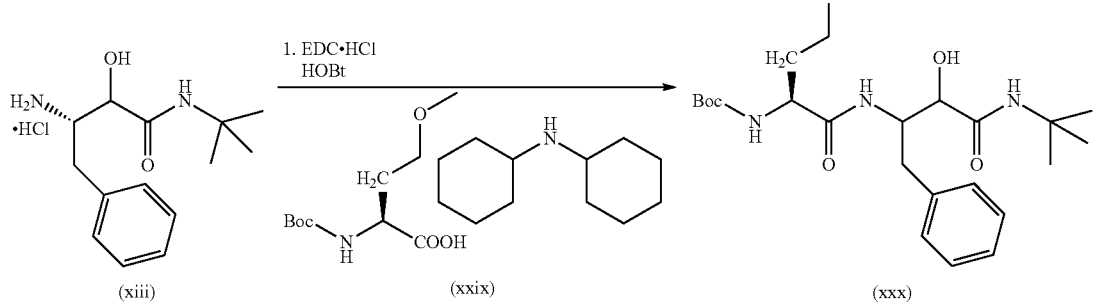

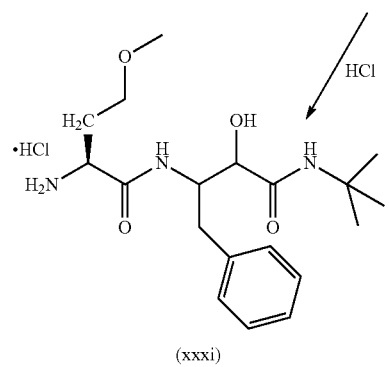

(xxxi)

Title compound was obtained following a similar procedure to that described in reference example 8 but using compound (xiii) and the dicyclohexylamine salt of (2S)-tert-butoxycarbonylamino-4-methoxy-butyric acid (xxix) as the starting materials (250 mg, quantitative yield)

LC-MS (Method B): tR=1.6-1.75 min; m/z=366 (MH⁺).

Reference Example 12: (S)-2-amino-N—((S)-4-(tert-butylamino)-3,4-dioxo-1-phenylbutan-2-yl)hexanamide hydrochloride (xxxiv)

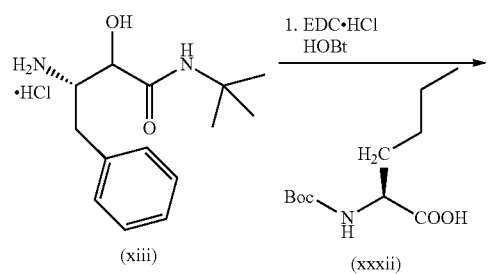

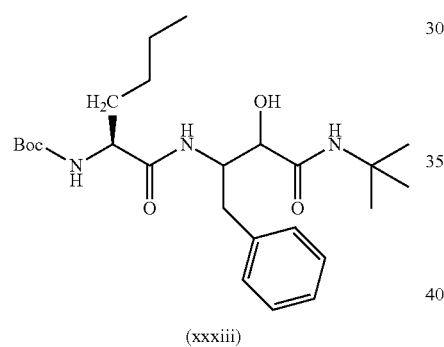

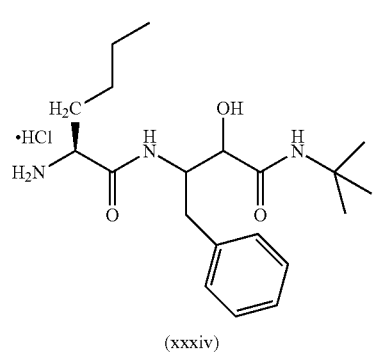

Title compound was obtained following a similar procedure to that described in reference example 8 but using compound (xiii) and (2S)-tert-Butoxycarbonylaminohexanoic acid (xxxiii) as the starting materials (315, quantitative yield).

LC-MS (Method B): tR=1.72-1.82 min; m/z=364 (MH⁺).

Reference Example 13: Tert-butyl 4-(((2S)-1-((4-(tert-butylamino)-3,4-dioxo-1-phenylbutan-2-yl)amino)-4-methyl-1-oxopentan-2-yl)carbamoyl)piperidine-1-carboxylate (xxxix)

Step-1: 4-[1-(1-Benzyl-2-tert-butylcarbamino-2-hydroxy-ethylcarbamoyl)-3-methyl-butylcarbamoyl]-piperidine-1-carboxylic acid tert-butyl ester (xxxviii)

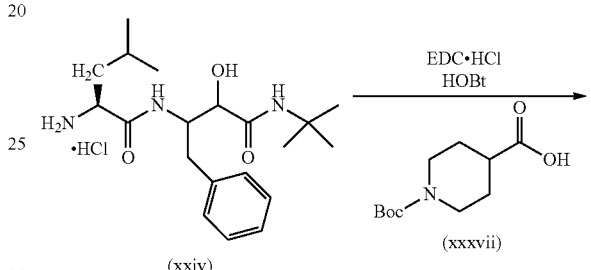

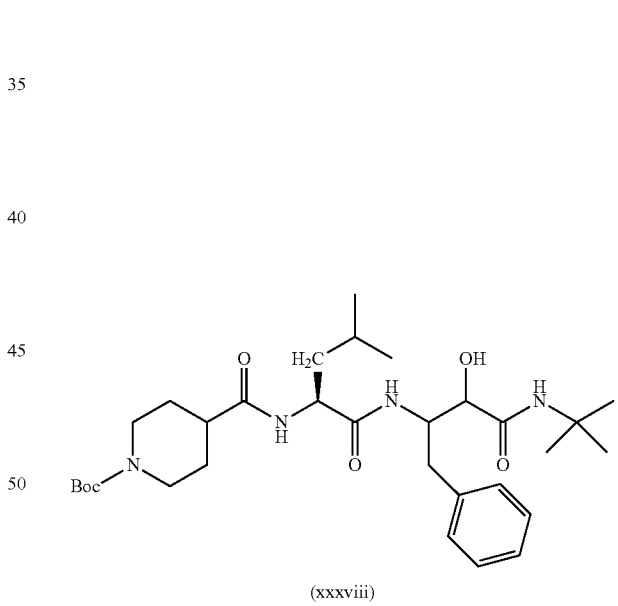

1-(tert-butoxy-carbonyl)piperidine-4-carboxylic acid (xxxvii) (37 mg, 1.5 eq), EDC.HCl (41 mg, 2 eq), HOBt.H₂O (32 mg, 2 eq) and compound (xxiv) (50 mg, 0.11 mmol) were dissolved in DCM (1 ml) then, DIPEA (3 eq) was added. Mixture was stirred for 16 hours at room temperature.

Solvent was then evaporated and crude was purified on ISCO Rf using Hexane and EtOH as mobile phase. Title compound got out at 4% EtOH (52 mg, 84% yield).

LC-MS (Method B): tR=2.83 min; m/z=576 (MH⁺)

Step-2: Tert-butyl 4-(((2S)-1-((4-(tert-butylamino)-3,4-dioxo-1-phenylbutan-2-yl)amino)-4-methyl-1-oxopentan-2-yl)carbamoyl)piperidine-1-carboxylate (xxxix)

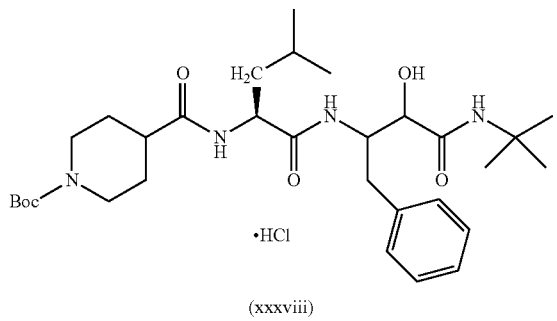

(xxxviii)

↓ Dess-Martin Periodinane

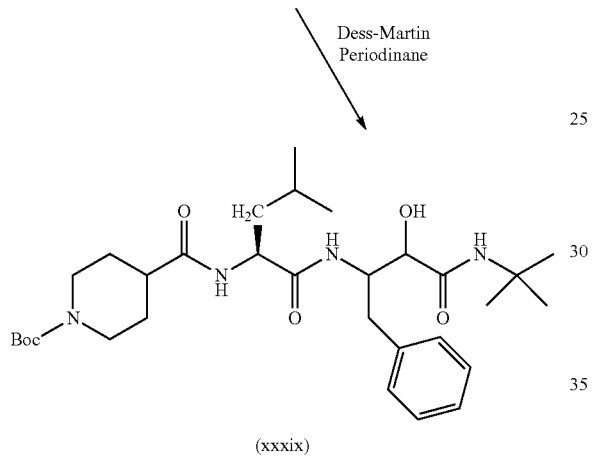

(xxxix)

Compound (xxxviii) obtained in step 1 was dissolved in DCM. Then, Dess-Martin periodinane was added. The mixture was stirred at this temperature for 2 hours. The solvent evaporated and the product was purified on ISCO Rf using Hexane and EtOH as solvents. Title compound got out at 2% EtOH (33 mg, 72% yield)

LC-MS (Method B): tR=3.07 min; m/z=574 (MH⁺).

Reference Example 14: (3S)-3-amino-2-hydroxy-N-methoxy-4-phenylbutanamide hydrochloride (xlii)

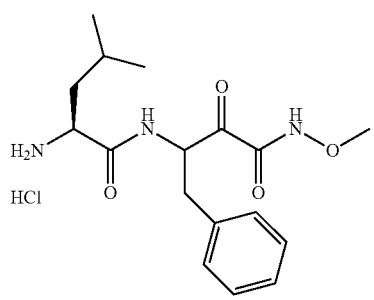

(xlii)

Title compound was obtained following a similar procedure to that described for reference example 3 but using methoxyamine instead of tert-amylamine as starting material.

Example 1: N-((2S)-1-((4-(ethylamino)-3,4-dioxo-1-phenylbutan-2-yl)amino)-4-methyl-1-oxopentan-2-yl)benzamide (1)

Step-1: N-((2S)-1-((4-(ethylamino)-3-hydroxy-4-oxo-1-phenylbutan-2-yl)amino)-4-methyl-1-oxopentan-2-yl) benzamide (xxxvi)

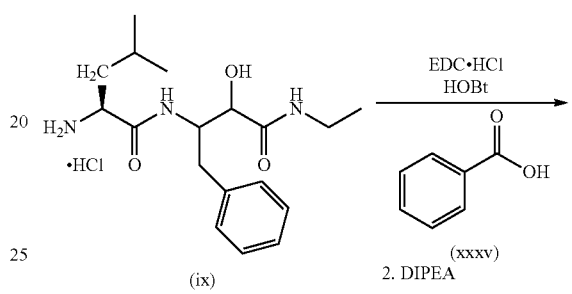

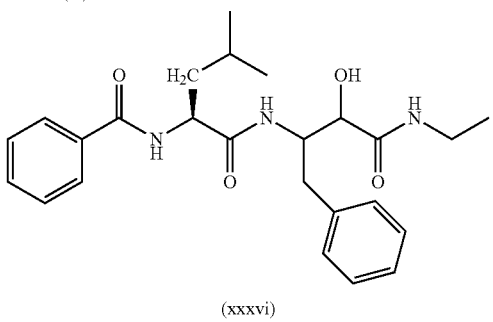

(xxxvi)

Benzoic acid (xxxv) (21.3 mg, 1.3 eq), EDC.HCl (38.7 mg, 1.5 eq), HOBt (31 mg, 1.5 eq) and compound (ix) (50 mg, 0.134 mmol) were dissolved in DCM (1 ml) then, DIPEA (3 eq) was added. Mixture was stirred for 2 hours at room temperature.

Solvent was then evaporated and crude was purified on ISCO Rf using Hexane and EtOH as mobile phase. Title compound got out at 30% EtOH (49 mg, 83% yield).

LC-MS (Method B): tR=2.63 min; m/z=440 (MH⁺)

Step-2: N-((2S)-1-((4-(ethylamino)-3,4-dioxo-1-phenylbutan-2-yl)amino)-4-methyl-1-oxopentan-2-yl)benzamide (1)

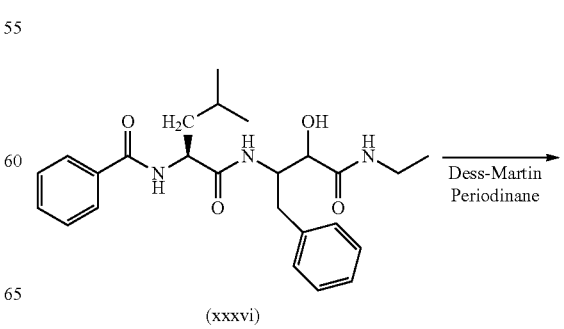

(xxxvi)

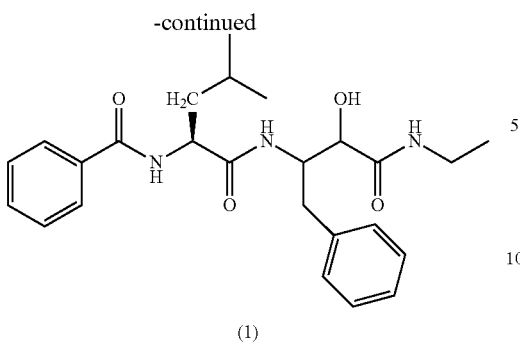

(1)

Compound (xxxvi) obtained in step 1 was dissolved in DCM. Then, Dess-Martin periodinane was added. The mixture was stirred at this temperature for 2 hours. The solvent evaporated and the product was purified on ISCO Rf using Hexane and EtOH as solvents.

Product was re-purified using a HLB cartridge on basic conditions (42.5 mg, 87% yield)

LC-MS (Method B): tR=2.65 min; m/z=438 (MH$^+$).

Examples 2-20

The compounds of examples 2-20 were obtained following a procedure similar to that described in example 1 but using the corresponding starting materials indicated in the table.

For each compound the table provides the chemical (IUPAC) name, the compounds of formulae (III) and (V) used to manufacture the compounds following the process described in Example 1, the LC-MS method used to determine the retention time and ratio mass/charge of the compound, the retention time and the ration mass/charge (MH$^+$) of the compound.

| Example | Name | Starting materials | Method (LC-MS) | $t_R$ (min) | m/z (MH+) |
|---|---|---|---|---|---|
| 2 | N-((2S)-1-((4-(ethylamino)-3,4-dioxo-1-phenylbutan-2-yl)amino)-4-methyl-1-oxopentan-2-yl)nicotinamide | Compound (ix) and Nicotinic Acid | B | 2.18 | 439 |
| 3 | (2S)-2-(3-cyclohexylpropanamido)-N-(4-(ethylamino)-3,4-dioxo-1-phenylbutan-2-yl)-4-methylpentanamide | Compound (ix) and 3-cyclohexyl-propionic acid | B | 3.07 | 472 |
| 4 | N-((2S)-1-((4-(ethylamino)-3,4-dioxo-1-phenylbutan-2-yl)amino)-4-methyl-1-oxopentan-2-yl)picolinamide | Compound (ix) and picolinic acid | B | 2.57 | 439 |
| 5 | N-((2S)-1-((4-(ethylamino)-3,4-dioxo-1-phenylbutan-2-yl)amino)-4-methyl-1-oxopentan-2-yl)isonicotinamide | Compound (ix) and isonicotinic acid | B | 2.2 | 439 |
| 6 | N-((2S)-1-((4-(ethylamino)-3,4-dioxo-1-phenylbutan-2-yl)amino)-4-methyl-1-oxopentan-2-yl)pyrimidine-5-carboxamide | Compound (ix) and pyrimidine-5-carboxylic acid | A | 2.28-2.5 | 440 |
| 7 | N-((2S)-1-((4-(tert-butylamino)-3,4-dioxo-1-phenylbutan-2-yl)amino)-4-methyl-1-oxopentan-2-yl)-3-methoxybenzamide | Compound (xxiv) and 3-methoxy-benzoic acid | B | 2.98 | 496 |
| 8 | N-((2S)-1-((4-(tert-butylamino)-3,4-dioxo-1-phenylbutan-2-yl)amino)-4-methyl-1-oxopentan-2-yl)pyrimidine-5-carboxamide | Compound (xxiv) and 5-pyrimidine-carboxylic acid | B | 2.53 | 468 |
| 9 | N-((2S)-1-((4-(tert-butylamino)-3,4-dioxo-1-phenylbutan-2-yl)amino)-4-methyl-1-oxopentan-2-yl)-2-chlorobenzamide | Compound (xxiv) and 2-chloro-benzoic acid | B | 3.00 | 500 |
| 10 | N-((2S)-1-((4-(tert-butylamino)-3,4-dioxo-1-phenylbutan-2-yl)amino)-4-methyl-1-oxopentan-2-yl)quinoline-3-carboxamide | Compound (xxiv) and quinoline-3-carboxylic acid | B | 2.85 | 517 |
| 11 | N-((2S)-1-((4-(tert-butylamino)-3,4-dioxo-1-phenylbutan-2-yl)amino)-4-methyl-1-oxopentan-2-yl)isoquinoline-5-carboxamide | Compound (xxiv) and isoquinoline-5-carboxylic acid | B | 2.70 | 517 |
| 12 | N-((2S)-1-((4-(tert-butylamino)-3,4-dioxo-1-phenylbutan-2-yl)amino)-4- | Compound (xxiv) and 2-chloro-6-methylbenzoic | B | 3.07 | 514 |

| Example | Name | Starting materials | Method (LC-MS) | $t_R$ (min) | m/z (MH+) |
|---|---|---|---|---|---|
| | methyl-1-oxopentan-2-yl)-2-chloro-6-methylbenzamide | acid | | | |
| 13 | N-((2S)-1-((4-(tert-butylamino)-3,4-dioxo-1-phenylbutan-2-yl)amino)-4-methyl-1-oxopentan-2-yl)pyridazine-3-carboxamide | Compound (xxiv) and 3-pyridazine-carboxylic acid | B | 2.65 | 468 |
| 14 | N-((2S)-1-((4-(tert-butylamino)-3,4-dioxo-1-phenylbutan-2-yl)amino)-4-methyl-1-oxopentan-2-yl)-2-methylbenzamide | Compound (xxiv) and o-toluic acid | B | 3.02 | 480 |
| 15 | N-((2S)-1-((4-(tert-butylamino)-3,4-dioxo-1-phenylbutan-2-yl)amino)-4-methyl-1-oxopentan-2-yl)pyrazine-2-carboxamide | Compound (xxiv) and 2-pyrazinecarboxylic acid | B | 2.70 | 468 |
| 16 | N-((2S)-1-((4-(cyclopropylamino)-3,4-dioxo-1-phenylbutan-2-yl)amino)-4-methyl-1-oxopentan-2-yl)nicotinamide | Compound (xxvi) and nicotinic acid | B | 2.23 | 451 |
| 17 | N-((2S)-1-((4-(cyclopropylamino)-3,4-dioxo-1-phenylbutan-2-yl)amino)-4-methyl-1-oxopentan-2-yl)pyrimidine-5-carboxamide | Compound (xxvi) and 5-pyrimidine-carboxylic acid | B | 2.15 | 452 |
| 18 | N-((2S)-1-((4-(tert-butylamino)-3,4-dioxo-1-phenylbutan-2-yl)amino)-4-methyl-1-oxopentan-2-yl)benzamide | Compound (xiii) and N-Benzoyl-L-leucine | B | 2.97 | 466 |
| 19 | N-((2S)-1-(4-(tert-butylamino)-3,4-dioxo-1-phenylbutan-2-ylamino)-4-methyl-1-oxopentan-2-yl)-5-methylnicotinamide | Compound (xxiv) and 5-methylicotinic acid | B | 2.72 | 481 |
| 20 | N-((2S)-1-((4-(cyclopropylamino)-3,4-dioxo-1-phenylbutan-2-yl)amino)-4-methyl-1-oxopentan-2-yl)benzamide | Compound (xvi) and N-Benzoyl-L-leucine | B | 2.63 | 451 |

Example 21: N-((2S)-1-((4-(tert-butylamino)-3,4-dioxo-1-phenylbutan-2-yl)amino)-4-methyl-1-oxopentan-2-yl)nicotinamide Step-1: N-((2S)-1-((4-(tert-butylamino)-3-hydroxy-4-oxo-1-phenylbutan-2-yl)amino)-4-methyl-1-oxopentan-2-yl)nicotinamide (xxxviii)

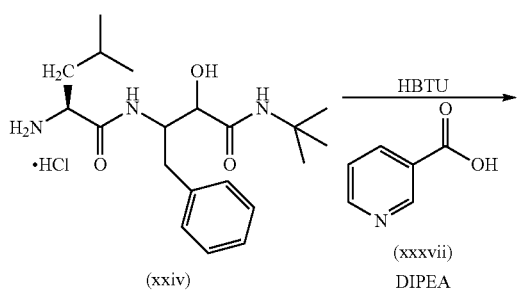

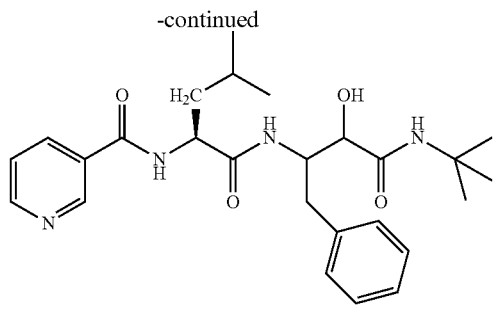

(xxxviii)

HBTU (343 mg, 0.89 mmol) was added to a solution of nicotinic acid (xxxvii) (100 mg, 0.812 mmol) in anhydrous DCM (5 mL). After 15 min, a solution of compound (xxiv) (253 mg, 0.54 mmol) and DIPEA (0.46 mL, 2.68 mmol) in anhydrous DCM (3 ml) were added and the resulting mixture was stirred at room temperature. After 3 h, volatiles were removed under vacuum and crude extracted in EtOAc washing with NaHCO$_3$ aq sat sol (15 mL) and solvent removed under vacuum.

The product was purified through column chromatography: ISCO (40 g, Hexanes/EtOH, from 2 to 10% in EtOH. Product eluted at 10% in EtOH. 124 mg were obtained (49% yield).

LC-MS (Method B): tR=2.30-2.37 min; m/z=470 (MH$^+$)

Step-2: N-((2S)-1-((4-(tert-butylamino)-3,4-dioxo-1-phenylbutan-2-yl)amino)-4-methyl-1-oxopentan-2-yl)nicotinamide (21)

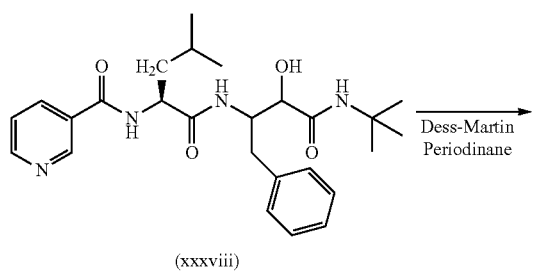

(xxxviii)

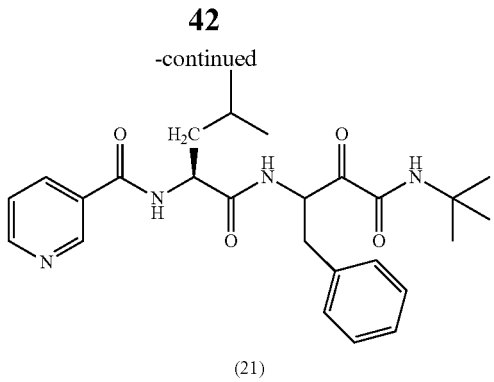

(21)

Preparation took place in a manner analogous to Example 1 Step 2 using compound (xxxviii) (124 mg) as the starting material. 96.1 mg were obtained (79% yield).

LC-MS (Method B): tR=2.58 min; m/z=467 (MH$^+$).

Examples 22-62

The compounds of examples 22-62 were obtained following a procedure similar to that described in example 1 but using the corresponding starting materials indicated in the table.

For each compound the table provides the chemical (IUPAC) name, the compounds of formulae (III) and (V) used to manufacture the compounds following the process described in Example 21, the LC-MS method used to determine the retention time and ratio mass/charge of the compound, the retention time and the ration mass/charge (MH$^+$) of the compound.

| Example | Name | Starting materials | Method (LC-MS) | $t_R$ (min) | m/z (MH$^+$) |
|---|---|---|---|---|---|
| 22 | N-((2S)-1-((4-(tert-butylamino)-3,4-dioxo-1-phenylbutan-2-yl)amino)-4-methyl-1-oxopentan-2-yl)isonicotinamide | Compound (xxiv) and isonicotinic acid | B | 2.60 | 467 |
| 23 | N-((2S)-1-((4-(tert-butylamino)-3,4-dioxo-1-phenylbutan-2-yl)amino)-4-methyl-1-oxopentan-2-yl)-4-cyanobenzamide | Compound (xxiv) and 4-cyano-benzoic acid | B | 2.90 | 491 |
| 24 | N-((2S)-1-((4-(tert-butylamino)-3,4-dioxo-1-phenylbutan-2-yl)amino)-4-methyl-1-oxopentan-2-yl)-3,5-dimethylbenzamide | Compound (xxiv) and 3,5-dimethyl-benzoic acid | B | 3.22 | 494 |
| 25 | N-((2S)-1-((4-(tert-butylamino)-3,4-dioxo-1-phenylbutan-2-yl)amino)-4-methyl-1-oxopentan-2-yl)-6-methylnicotinamide | Compound (xxiv) and 6-methyl-nicotinic acid | B | 2.67 | 481 |
| 26 | N-((2S)-1-(4-(tert-butylamino)-3,4-dioxo-1-phenylbutan-2-ylamino)-4-methyl-1-oxopentan-2-yl)pyrimidine-4-carboxamide | Compound (xxiv) and pyrimidine-4-carboxylic acid | A | 3.07 | 468 |
| 27 | N-((2S)-1-(4-(tert-butylamino)-3,4-dioxo-1-phenylbutan-2-ylamino)-4-methyl-1-oxopentan-2-yl)-2-methylnicotinamide | Compound (xxiv) and 2-methyl-nicotinic acid | A | 2.57 | 481 |
| 28 | N-((2S)-1-(4-(tert-butylamino)-3,4-dioxo-1-phenylbutan-2-ylamino)-4-methyl-1-oxopentan-2-yl)tetrahydro-2H-pyran-4-carboxamide | Compound (xxiv) and tetrahydro-2H-pyran-4-carboxylic acid | A | 2.92 | 474 |

-continued

| Example | Name | Starting materials | Method (LC-MS) | $t_R$ (min) | m/z (MH$^+$) |
|---|---|---|---|---|---|
| 29 | N-((2S)-1-(4-(tert-butylamino)-3,4-dioxo-1-phenylbutan-2-ylamino)-4-methyl-1-oxopentan-2-yl)picolinamide | Compound (xxiv) and picolinic acid | B | 2.93 | 467 |
| 30 | N-((2S)-1-(4-(cyclohexylamino)-3,4-dioxo-1-phenylbutan-2-ylamino)-4-methyl-1-oxopentan-2-yl)benzamide | Compound (xix) and N-Benzoyl-L-leucine | A | 3.33 | 492 |
| 31 | N-((2S)-1-(4-(tert-butylamino)-3,4-dioxo-1-phenylbutan-2-ylamino)-4-methyl-1-oxopentan-2-yl)-5-fluoronicotinamide | Compound (xxiv) and 5-fluoro-nicotinic acid | A | 3.07 | 485 |
| 32 | N-((2S)-1-(4-(tert-butylamino)-3,4-dioxo-1-phenylbutan-2-ylamino)-4-methyl-1-oxopentan-2-yl)-6-(trifluoromethyl)nicotinamide | Compound (xxiv) and 6-(trifluoromethyl)nicotinic acid | A | 3.30 | 535 |
| 33 | N-((2S)-1-(4-(tert-butylamino)-3,4-dioxo-1-phenylbutan-2-ylamino)-4-methyl-1-oxopentan-2-yl)-2-methyl-6-(trifluoromethyl)nicotinamide | Compound (xxiv) and 2-methyl-6-(trifluoromethyl)nicotinic acid | A | 3.33 | 549 |
| 34 | N-((2S)-1-(4-(tert-butylamino)-3,4-dioxo-1-phenylbutan-2-ylamino)-4-methyl-1-oxopentan-2-yl)-4-methylnicotinamide | Compound (xxiv) and 4-methyl-nicotinic acid | A | 2.68 | 481 |
| 35 | N-((2S)-1-(4-(tert-butylamino)-3,4-dioxo-1-phenylbutan-2-ylamino)-4-methyl-1-oxopentan-2-yl)-4-fluorobenzamide | Compound (xxiv) and 4-fluoro-benzoic acid | A | 3.28 | 484 |
| 36 | N-((2S)-1-(4-(tert-butylamino)-3,4-dioxo-1-phenylbutan-2-ylamino)-4-methyl-1-oxopentan-2-yl)-4-chloro-2-fluorobenzamide | Compound (xxiv) and 4-chloro-2-fluoro-benzoic acid | A | 3.48 | 518 |
| 37 | N-((2S)-1-(4-(tert-butylamino)-3,4-dioxo-1-phenylbutan-2-ylamino)-4-methyl-1-oxopentan-2-yl)-4-chloronicotinamide | Compound (xxiv) and 4-chloronicotinic acid | A | 3.02 | 501 |
| 38 | N-((2S)-1-(4-(tert-butylamino)-3,4-dioxo-1-phenylbutan-2-ylamino)-3-cyclopropyl-1-oxopropan-2-yl)nicotinamide | Compound (xxviii) and nicotinic acid | A | 2.75 | 465 |
| 39 | N-((2S)-1-(4-(tert-butylamino)-3,4-dioxo-1-phenylbutan-2-ylamino)-3-cyclopropyl-1-oxopropan-2-yl)benzamide | Compound (xxviii) and Ben-zoic acid | A | 3.17 | 464 |
| 40 | N-((2S)-1-(4-(tert-butylamino)-3,4-dioxo-1-phenylbutan-2-ylamino)-4-methyl-1-oxopentan-2-yl)-5-chloronicotinamide | Compound (xxiv) and 5-chloro-nicotinic acid | A | 3.20 | 501 |
| 41 | N-((2S)-1-(4-(tert-butylamino)-3,4-dioxo-1-phenylbutan-2-ylamino)-4-methyl-1-oxopentan-2-yl)-3-chloro-2-fluorobenzamide | Compound (xxiv) and 3-chloro-2-fluorobenzoic acid | A | 3.43 | 518 |
| 42 | N-((2S)-1-(4-(tert-butylamino)-3,4-dioxo-1-phenylbutan-2-ylamino)-4-methoxy-1-oxobutan-2-yl)nicotinamide | Compound (xxxi) and nicotinic acid | A | 2.53 | 469 |
| 43 | N-((2S)-1-(4-(tert-butylamino)-3,4-dioxo-1-phenylbutan-2-ylamino)-4-methoxy-1-oxobutan-2-yl)benzamide | Compound (xxxi) and benzoic acid | A | 2.97 | 468 |

-continued

| Example | Name | Starting materials | Method (LC-MS) | $t_R$ (min) | m/z (MH+) |
|---|---|---|---|---|---|
| 44 | N-((2S)-1-(4-(tert-butylamino)-3,4-dioxo-1-phenylbutan-2-ylamino)-1-oxohexan-2-yl)nicotinamide | Compound (xxxiv) and nicotinic acid | A | 2.85 | 467 |
| 45 | N-((2S)-1-(4-(tert-butylamino)-3,4-dioxo-1-phenylbutan-2-ylamino)-1-oxohexan-2-yl)benzamide | Compound (xxxiv) and benzoic acid | A | 3.25 | 466 |
| 46 | N-((2S)-1-(4-(tert-butylamino)-3,4-dioxo-1-phenylbutan-2-ylamino)-4-methyl-1-oxopentan-2-yl)-4-chloro-2-methylbenzamide | Compound (xxiv) and 4-chloro-2-methylbenzoic acid | A | 3.47 | 514 |
| 47 | N-((2S)-1-(4-(tert-butylamino)-3,4-dioxo-1-phenylbutan-2-ylamino)-4-methyl-1-oxopentan-2-yl)-4-(dimethylamino)benzamide | Compound (xxiv) and 4-(dimethyl-amino) benzoic acid | A | 3.28 | 509 |
| 48 | N-((2S)-1-(4-(tert-butylamino)-3,4-dioxo-1-phenylbutan-2-ylamino)-4-methyl-1-oxopentan-2-yl)-6-hydroxynicotinamide | Compound (xxiv) and 6-hydroxynicotinic acid | A | 2.56 | 483 |
| 49 | N-((2S)-1-((4-(tert-butylamino)-3,4-dioxo-1-phenylbutan-2-yl)amino)-4-methyl-1-oxopentan-2-yl)cyclopentanecarboxamide | Compound (xxiv) and cyclopentane-carboxylic acid | A | 3.25 | 458 |
| 50 | N-((2S)-1-((3,4-dioxo-4-(tert-pentylamino)-1-phenylbutan-2-yl)amino)-4-methyl-1-oxopentan-2-yl)benzamide | Ref Ex 3 and N-Benzoyl-L-leucine | A | 3.35 | 480 |
| 51 | N-((2S)-1-(4-(tert-butylamino)-3,4-dioxo-1-phenylbutan-2-ylamino)-4-methyl-1-oxopentan-2-yl)-2-hydroxynicotinamide | Compound (xxiv) and 2-hydroxy-nicotinic acid | A | 2.75 | 483 |
| 52 | N-[(1S)-1-(1-benzyl-2-tert-butylcarbamoyl-2-oxo-ethylcarbamoyl)-3-methyl-butyl]-benzamide | Compound (ix) and benzoic acid | B | 2.21 | 467 |
| 53 | N-[(1S)-1-(1-benzyl-2-cyclopropylcarbamoyl-2-oxo-ethylcarbamoyl)-3-methyl-butyl]-benzamide | Compound (xxvi) and benzoic acid | B | 2.18 | 451 |
| 54 | Quinoline-3-carboxylic acid [(1S)-1-(1-benzyl-2-tert-butylcarbamoyl-2-oxo-ethylcarbamoyl)-3-methyl-butyl]-amide | Compound (xxiv) and 3-quinolinecarboxylic acid | B | 2.65 | 517 |
| 55 | Pyridazine-3-carboxylic acid [(1S)-1-(1-benzyl-2-tert-butylcarbamoyl-2-oxo-ethylcarbamoyl)-3-methyl-butyl]-amide | Compound (xxiv) and pyridazine-3-carboxylic acid | B | 2.11 | 469 |
| 56 | N-[(1S)-1-(1-benzyl-2-tert-butylcarbamoyl-2-oxo-ethylcarbamoyl)-3-methyl-butyl]-2-methyl-benzamide | Compound (xxiv) and o-toluic acid | B | 2.68 | 481 |
| 57 | Tetrahydro-pyran-4-carboxylic acid [(1S)-1-(1-benzyl-2-tert-butylcarbamoyl-2-oxo-ethylcarbamoyl)-3-methyl-butyl]-amide | Compound (xxiv) and tetrahydropyran-4-yl-carboxylic acid | B | 2.05 | 475 |
| 58 | N-[(1S)-1-(1-benzyl-2-cyclohexylcarbamoyl-2-oxo-ethylcarbamoyl)-3-methyl-butyl]-benzamide | Compound (xix) and N-benzoyl-L-leucine | B | 2.67 | 492 |
| 59 | N-[(1S)-1-(1-benzyl-2-benzylcarbamoyl-2-oxo-ethylcarbamoyl)-3-methyl-butyl]-benzamide | Compound (xxii) and N-benzoyl-L-leucine | B | 2.33 | 500 |
| 60 | N-[(1S)-1-(1-benzyl-2-tert-butylcarbamoyl-2-oxo- | Compound (xxiv) and 4- | B | 2.43 | 502 |

-continued

| Example | Name | Starting materials | Method (LC-MS) | $t_R$ (min) | m/z (MH+) |
|---|---|---|---|---|---|
| 61 | ethylcarbamoyl)-3-methyl-butyl]-4-chloro-nicotinamide N-[(1S)-1-(1-benzyl-2-methoxycarbamoyl-2-oxo-ethylcarbamoyl)-3-methyl-butyl]-3-methoxy-benzamide | chloropyridine-3-carboxylic acid Compound (xlii) and 3-methoxybenzoic acid | B | 2.64 | 471 |
| 62 | Benzo[1,3]dioxole-5-carboxylic acid [(1S)-1-(1-benzyl-2-methoxycarbamoyl-2-oxo-ethylcarbamoyl)-3-methyl-butyl]-amide | Compound (xlii) and benzo[1,3]dioxole-5-carboxylic acid | B | 2.07 | 485 |

Example 63: N-((2S)-1-((4-(tert-butylamino)-3,4-dioxo-1-phenylbutan-2-yl)amino)-4-methyl-1-oxo-pentan-2-yl)piperidine-4-carboxamide hydrochloride Example 64: tert-butyl (2S)-1-(4-(ethylamino)-3,4-dioxo-1-phenylbutan-2-ylamino)-4-methyl-1-oxo-pentan-2-ylcarbamate

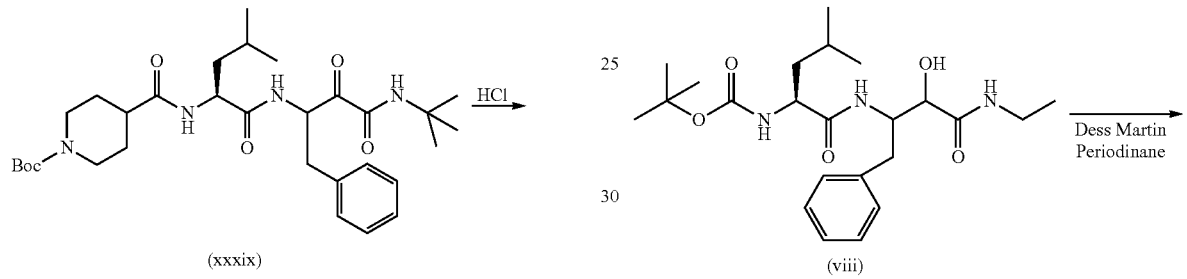

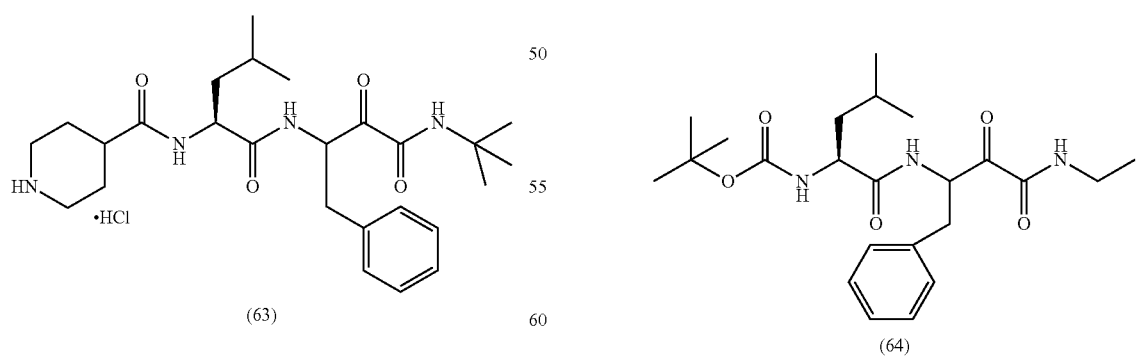

HCl 4 N in 1,4-Dioxane was added to compound (xxxix) of Reference example 13 and the mixture was stirred at room temperature for 3 h. The crude was concentrated. 23.2 mg were obtained (quantitative yield).

LC-MS (Method B): tR=2.28 min; m/z=474 (MH+).

Preparation took place in a manner analogous to Example 1 Step 2 using compound (viii) (100 mg) as the starting material. 69 mg were obtained (69% yield).

LC-MS (Method B): tR=2.34 min; m/z=434 (MH+).

Example 65: (2S)-2-(3-tert-butylureido)-N-(4-(ethylamino)-3,4-dioxo-1-phenylbutan-2-yl)-4-methylpentanamide

Step-1: (2S)-2-(3-tert-butylureido)-N-(4-(ethylamino)-3-hydroxy-4-oxo-1-phenylbutan-2-yl)-4-methylpentanamide (xl)

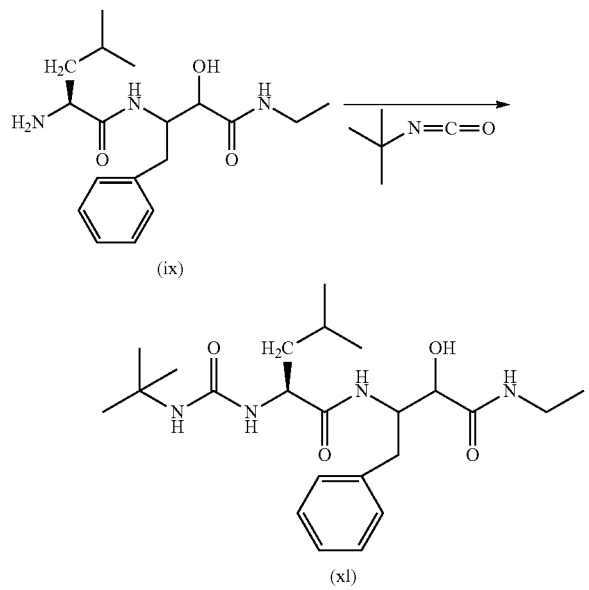

(2S)-2-amino-N-(4-(ethylamino)-3-hydroxy-4-oxo-1-phenylbutan-2-yl)-4-methylpentanamide (ix) (40 mg, 0.12 mmol), 2-isocyanato-2-methylpropane (18 µL, 0.16 mmol) and potassium carbonate (49 mg, 0.36 mmol) were dissolved in acetonitrile (1 ml). Mixture was stirred at room temperature for 2 hours. Solvent was evaporated under reduced pressure. Product was purified through column chromatography: ISCO (12 g), Hexanes/EtOH, from 10 to 30% in EtOH. Product eluted at 30% in EtOH. 19 mg were obtained (36% yield).

LC-MS (Method B): tR=2.35 min; m/z=435 (MH+).

Step-2: (2S)-2-(3-tert-butylureido)-N-(4-(ethylamino)-3,4-dioxo-1-phenylbutan-2-yl)-4-methylpentanamide

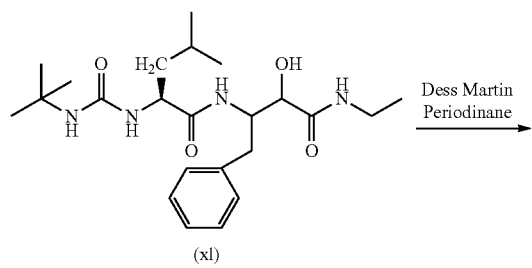

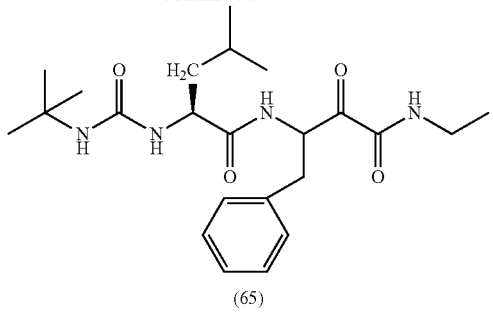

(2S)-2-(3-(tert-butyl)ureido)-N-(4-(ethylamino)-3-hydroxy-4-oxo-1-phenylbutan-2-yl)-4-methylpentanamide (xl) (19 mg, 0.04 mmol) was dissolved in DCM (1 mL). Dess Martin (3 eq), was added at room temperature and mixture was stirred for 2 hours. Solvent was evaporated under reduced pressure. Product was purified through column chromatography: ISCO Rf, Hexanes/EtOH, from 10 to 30% in EtOH. Product eluted at 20-25% in EtOH. 14 mg were obtained (74% yield).

LC-MS (Method B): tR=2.58 min; m/z=433 (MH+)

Example 66: 2-methoxyethyl ((2S)-1-((4-(ethylamino)-3,4-dioxo-1-phenylbutan-2-yl)amino)-4-methyl-1-oxopentan-2-yl)carbamate

Step-1: 2-methoxyethyl ((2S)-1-((4-(ethylamino)-3-hydroxy-4-oxo-1-phenylbutan-2-yl)amino)-4-methyl-1-oxopentan-2-yl)carbamate (lii)

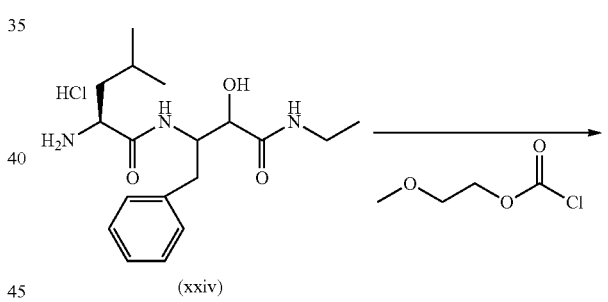

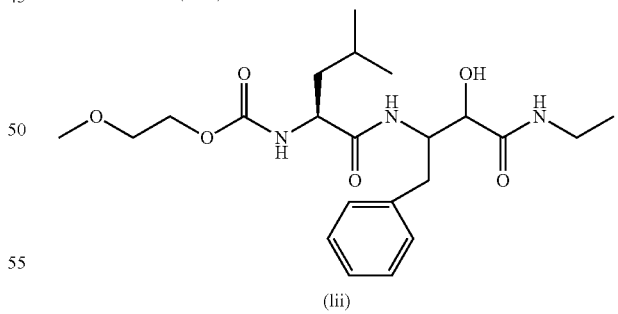

Compound (xxiv) (40 mg, 0.12 mmol) was dissolved in DCM (1 ml) and DIPEA (21 µl, 0.12 mmol) was added. Then, 2-methoxyethyl carbonochloridate (21 µl, 0.12 mmol) was added and mixture was stirred for 2 hours at room temperature. Solvent was evaporated. Product was purified through column chromatography: ISCO (12 g, Hexanes/EtOH) from 2 to 10% in EtOH. Product eluted at 8% in EtOH. 58 mg were obtained (quantitative yield).

LC-MS (Method B): tR=2.12 min; m/z=438 (MH+)

Step-2: 2-methoxyethyl ((2S)-1-((4-(ethylamino)-3, 4-dioxo-1-phenylbutan-2-yl)amino)-4-methyl-1-oxopentan-2-yl)carbamate (66)

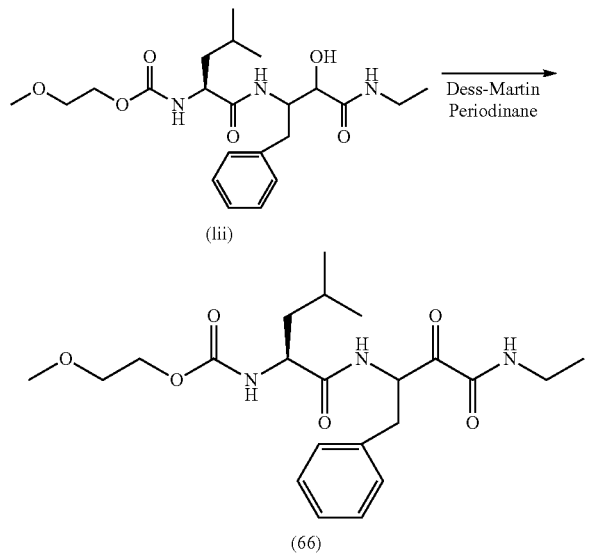

Preparation took place in a manner analogous to Example 1 Step 2 using compound (lii) (58 mg) as the starting material. Product was purified through column chromatography: ISCO (12 g, Hexanes/EtOH) from 1 to 5% in EtOH. Product eluted at 3% in EtOH Product was further purified using a HLB cartridge on basic conditions (10 mM $NH_4CO_3$ aqueous solution of pH=9 (A) and acetonitrile (B)). 18.6 mg were obtained (32% yield).

LC-MS (Method B): tR=2.33 min; m/z=436 (MH$^+$).

Example 67. [(1S)-1-(1-benzyl-2-methoxycarbamoyl-2-oxo-ethylcarbamoyl)-3-methyl-butyl]-carbamic acid 2-methoxy-ethyl ester The compound of example 66 was obtained following a procedure similar to that described in example 65 but using compound (xlii) instead of compound (xxiv).

LC-MS (Method B): tR=2.51 min; m/z=438 (MH$^+$).

Biological Data
Mouse 3T3-L1 Pre-Adipocyte Cells Differentiation Assay
Cell Culture and Treatment Mouse (*Mus musculus*) 3T3-L1 pre-adipocyte cell line was purchased at ATCC.

Induction of adipocyte differentiation was performed according to Choi K C et al "The role of ghrelin and growth hormone secretagogues receptor on rat adipogenesis" Endocrinol 144: 754-759, 2003 with some modifications.

Briefly, 3T3-L1 pre-adipocytes were seeded in 24 well culture plates at a density of $3\times10^4$ cells/well in growth medium (DMEM containing 4.5 g/L glucose, 1 mM sodium pyruvate, 2 mM L-glutamine, 100 µg/mL streptomycin/penicilline, 25 mM HEPES and 10% calf serum (heat inactivated)). The resulting solution is used as a blank in the measure of fluorescence described below.

Cells were incubated at 37° C., 95% humidity and 10% $CO_2$. Two days after reaching confluence (ninth day) growth medium was changed to differentiation medium (DMEM containing 4.5 g/L glucose, 2 mM L-glutamine, 100 µg/mL streptomycin/penicilline, 25 mM HEPES, 10% FBS (heat inactivated), 1 mM sodium pyruvate, 0.5 mM 3-isobutyl-1-methylxanthine, 0.25 µM dexamethasone, and 5 µg/mL insulin). After 48 h, the medium was replaced by insulin medium (DMEM containing 4.5 g/L glucose, 1 mM sodium pyruvate, 2 mM L-glutamine, 100 µg/mL streptomycin/penicillin, 25 mM HEPES, 10% FBS (inactivated) and 5 µg/mL insulin) for another 48 hours, and then incubated in 10% FBS/DMEM (same as insulin medium without insulin) for 4 days up to their complete differentiation.

The compounds to be tested were added at the 25 µM concentration to the differentiation medium (2 days) and to the insulin medium (2 days).

After incubation, the intracellular stored lipids were quantified by measuring the fluorescence after staining the lipids with the fluorescent dye Nile Red (9-diethylamino-5-benzo[α]phenoxazinone).

To carry out said lipid measurement, cells were lysed in hypotonic buffer (1 mM Tris-HCl pH=7.5) containing 2 µg/ml of Nile Red (9-diethylamino-5-benzo[t]phenoxazinone) for 15 min at 37° C.

Lysed cells were homogenized and TAG content was determined by monitoring Nile Red fluorescence in a laser spectral fluorometer. Excitation 522 nm; Emission 574 nm.

For each compound to be tested the following fluorescence measures were recorded:

FC: Fluorescence of a sample of lysed cells incubated in the presence of the compound in both the differentiation medium and in the insulin medium.

FB: Fluorescence of a blank sample of sample of pre-adipocytes in growth medium.

FNC: Fluorescence of a sample of lysed cells incubated with the differentiation medium and insulin medium not comprising any additional compound.

The inhibition of adipogenesis in the presence of the tested compounds is calculated from the following equation:

% of adipogenesis inhibition=100−[100×((FC−FB)/(FNC−FB))]

% of adipogenesis inhibition (reflecting the activity against 3T3-L1 cell differentiation into adipocytes) was determined for each compound, and the effect at the M concentration has been chosen as the most representative value as to be shown in the structure-activity table.

The table below summarises the results obtained for the tested compounds. In the table the following symbols have been used to represent % of adipogenesis inhibition:
Inhibition between >1% and 15% → +
Inhibition between >15% and 30% → ++
Inhibition between >30% and 80% → +++

| Example | Adipogenesis inhibition score |
| --- | --- |
| 1 | ++ |
| 4 | + |
| 6 | ++ |
| 7 | ++ |
| 8 | + |
| 10 | +++ |
| 11 | +++ |
| 15 | + |
| 18 | ++ |
| 20 | +++ |
| 21 | + |
| 25 | +++ |
| 31 | + |

-continued

| Example | Adipogenesis inhibition score |
|---|---|
| 32 | +++ |
| 52 | ++ |
| 53 | +++ |
| 54 | +++ |
| 55 | ++ |
| 56 | ++ |
| 57 | ++ |
| 58 | +++ |
| 59 | +++ |
| 60 | +++ |
| 61 | +++ |
| 62 | +++ |
| 64 | +++ |
| 65 | ++ |
| 67 | ++ |

The results in table above show that the compounds of the invention are capable of inhibiting adipogenesis in pre-adipocyte cells.

The invention claimed is:
1. A compound of formula (II)

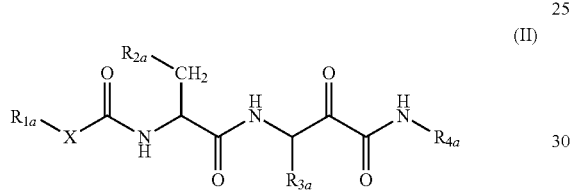

(II)

wherein
X is selected from the group consisting of a single bond, an oxygen atom and a —NH— group;
when X is O, $R_{1a}$ is selected from the group consisting of a1) $C_{1-8}$ alkyl, optionally substituted by one $C_{1-8}$ alkoxy group, b1) $C_{6-10}$ aryl-$C_{1-4}$ alkyl and c1) $C_{5-10}$ heteroaryl-$C_{1-4}$ alkyl wherein the $C_{5-10}$ heteroaryl ring system comprises 1 to 3 heteroatoms selected from the group consisting of nitrogen, oxygen and sulphur,
when X is a single bond, $R_{1a}$ is selected from the group consisting of d1) phenyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; f1) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NH_2$, CN, $CF_3$, $C_{1-6}$ linear or branched alkyl and halogen atoms; g1) $C_{1-6}$ linear or branched alkyl, optionally substituted by one $C_{1-8}$ alkoxy group; and h1) $C_{3-6}$ cycloalkyl-$C_{0-2}$ alkyl optionally substituted by 1 to 3 substituents selected from the group consisting of OH, $NR_5R_6$, CN, $CF_3$, $C_{1-6}$ linear or branched alkyl and halogen atoms;
when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NH_2$, CN, $CF_3$, $C_{1-6}$ linear or branched alkyl and halogen atoms; f2) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g2) $C_{1-6}$ linear or branched alkyl, optionally substituted by one $C_{1-8}$ alkoxy group and h2) $C_{3-6}$ cycloalkyl-$C_{0-2}$ alkyl optionally substituted by 1 to 3 substituents selected from the group consisting of OH, $NR_5R_6$, CN, $CF_3$, $C_{1-6}$ linear or branched alkyl and halogen atoms;
$R_{2a}$ is selected from the group consisting of ii) $C_{1-8}$-alkyl optionally substituted with 1, 2 or 3 fluor atoms, j1) $C_{1-8}$ alkoxy-$C_{1-8}$ alkyl, and k1) $C_{3-6}$ cycloalkyl-$C_{0-2}$ alkyl, wherein the cycloalkyl ring is optionally substituted with 1, 2 or 3 fluor atoms, with the proviso that when X is 0 then $R_{2a}$ is not an isopropyl group;
$R_{3a}$ is selected from the group consisting of l1) $C_{1-8}$-alkyl and m1) benzyl optionally substituted by 1 to 3 substituents selected from the group consisting of $C_{1-4}$-alkyl, MeO, CN and halogen atoms, with the proviso that when X is a single bond and $R_{1a}$ is a $C_{5-10}$ heterocyclyl-$C_{0-2}$ alkyl group, $R_{3a}$ is not an ethyl group;
$R_{4a}$ is selected from the group consisting of n1) $C_{1-8}$-alkyl, o1) $C_{3-6}$ cycloalkyl-$C_{0-2}$ alkyl optionally substituted by $C_{1-4}$-alkyl and p1) $C_{1-8}$-alkoxy; and
$R_5$ and $R_6$ are independently selected from the group consisting of hydrogen atoms and $C_{1-6}$ linear or branched alkyl groups;
or a pharmaceutically acceptable salt thereof.

2. A compound of formula (II) according to claim 1, wherein:
X is selected from the group consisting of a single bond, an oxygen atom and a —NH— group,
when X is O, $R_{1a}$ is selected from the group consisting of a1) $C_{1-8}$ alkyl, b1) $C_{6-10}$ aryl-$C_{1-4}$alkyl and c1) $C_{5-10}$ heteroaryl-$C_{1-4}$ alkyl wherein the $C_{5-10}$ heteroaryl ring system comprises 1 to 3 heteroatoms selected from the group consisting of nitrogen, oxygen and sulphur,
when X is a single bond, $R_{1a}$ is selected from the group consisting of d1) phenyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; f1) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g1) $C_{1-6}$ linear or branched alkyl and h1) $C_{3-6}$cycloalkyl-$C_{0-2}$alkyl optionally substituted by 1 to 3 substituents selected from the group consisting of OH, $NR_{5a}R_{6a}$, CN, $CF_3$, $C_{1-6}$ linear or branched alkyl and halogen atoms;

when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NR_{5a}R_{6a}$, CN, $CF_3$, $C_{1-6}$ linear or branched alkyl and halogen atoms; f2) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_{5a}R_{6a}$, CN, $CF_3$, $C_{1-6}$ linear or branched alkyl and halogen atoms; g2) $C_{1-6}$ linear or branched alkyl and h2) $C_{3-6}$ cycloalkyl-$C_{0-2}$ alkyl optionally substituted by 1 to 3 substituents selected from the group consisting of OH, $NH_2$, CN, $CF_3$, $C_{1-6}$ linear or branched alkyl and halogen atoms;

$R_{2a}$ is selected from the group consisting of ii) $C_{1-8}$ alkyl, j1) $C_{1-8}$ alkoxy-$C_{1-8}$ alkyl and k1) $C_{3-6}$ cycloalkyl-$C_{0-2}$ alkyl with the proviso that when X is 0 then $R_{2a}$ is not an isopropyl group;

$R_{3a}$ is selected from the group consisting of l1) $C_{1-8}$ alkyl and m1) benzyl optionally substituted by 1 to 3 substituents selected from the group consisting of $C_{1-4}$-alkyl, MeO, CN and halogen atoms with the proviso that when X is a single bond and $R_{1a}$ is a $C_{5-10}$ heterocyclyl-$C_{0-2}$ alkyl group, $R_{3a}$ is not an ethyl group;

$R_{4a}$ is selected from the group consisting of n1) $C_{1-8}$ alkyl and o1) $C_{3-6}$ cycloalkyl-$C_{0-2}$ alkyl optionally substituted by $C_{1-4}$ alkyl; and $R_{5a}$ and $R_{6a}$ are independently selected from the group consisting of hydrogen atoms and $C_{1-6}$ linear or branched alkyl groups;

or a pharmaceutically acceptable salt thereof.

3. A compound of formula (II) according to claim 1 wherein either (i) X is selected from the group consisting of O and NH and $R_{1a}$ is selected from the group consisting of a1) $C_{1-6}$ alkyl or ii) X is a single bond and the $R_{1a}$ group is selected from the group consisting of d1) phenyl optionally substituted by 1 to 3 substituents selected from the group consisting of CN, $CF_3$, $C_{1-3}$ linear or branched alkyl; and halogen atoms and f1) $C_{5-10}$ heterocyclyl wherein the heterocyclyl ring system is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen.

4. A compound of formula (II) according to claim 3, wherein X is a single bond.

5. A compound of formula (II) according to claim 1 wherein the $R_{2a}$ group is selected from the group consisting of $C_{2-5}$ linear or branched alkyl and $C_{3-5}$ cycloalkyl with the proviso that when X is O then $R_{2a}$ is not an isopropyl group.

6. A compound of formula (II) according to claim 1, wherein the $R_{2a}$ group is selected from the group consisting of isopropyl, propyl and cyclopropyl, with the proviso that when X is O then $R_{2a}$ is not an isopropyl group.

7. A compound of formula (II) according to claim 1, wherein the $R_{3a}$ group is benzyl optionally substituted by 1 to 3 substituents selected from the group consisting of $C_{1-4}$-alkyl, MeO, CN and halogen atoms.

8. A compound of formula (II) according to claim 1 wherein the $R_{3a}$ group is benzyl optionally substituted by 1 to 3 substituents selected from the group consisting of $C_{1-4}$ alkyl, MeO, CN and halogen atoms; and wherein the $R_{2a}$ group is selected from the group consisting of isopropyl, propyl and cyclopropyl, with the proviso that when X is O then $R_{2a}$ is not an isopropyl group.

9. A compound of formula (II) according to claim 1, wherein the $R_{4a}$ group is selected from the group consisting of $C_{2-5}$ linear or branched alkyl and $C_{3-5}$ cycloalkyl, both optionally substituted by $C_{1-4}$-alkyl.

10. A compound of formula (II) according to claim 9, wherein the $R_{4a}$ group is selected from the group consisting of ethyl, tert-butyl and cyclopropyl.

11. A compound according to claim 1, having the following formula:
N-[(1S)-1-(1-benzyl-2-methoxycarbamoyl-2-oxo-ethyl-carbamoyl)-3-methyl-butyl]-3-methoxy-benzamide.

12. A process for the preparation of a compound of formula (II) as defined in claim 1, which comprises the reaction of a compound of formula (IV) with Dess-Martin periodinane

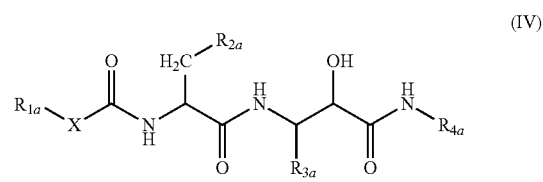

wherein—
X is selected from the group consisting of a single bond, an oxygen atom and a —NH— group;
when X is O, $R_{1a}$ is selected from the group consisting of a1) $C_{1-8}$ alkyl, optionally substituted by one $C_{1-8}$ alkoxy group, b1) $C_{6-10}$ aryl-$C_{1-4}$ alkyl and c1) $C_{5-10}$ heteroaryl-$C_{1-4}$ alkyl wherein the $C_{5-10}$ heteroaryl ring system comprises 1 to 3 heteroatoms selected from the group consisting of nitrogen, oxygen and sulphur,
when X is a single bond, $R_{1a}$ is selected from the group consisting of d1) phenyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; f1) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NH_2$, CN, $CF_3$, $C_{1-6}$ linear or branched alkyl and halogen atoms; g1) $C_{1-6}$ linear or branched alkyl, optionally substituted by one $C_{1-8}$ alkoxy group and h1) $C_{3-6}$ cycloalkyl-$C_{0-2}$ alkyl optionally substituted by 1 to 3 substituents selected from the group consisting of OH, $NR_5R_6$, CN, $CF_3$, $C_{1-6}$ linear or branched alkyl and halogen atoms;
when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NH_2$, CN, $CF_3$, $C_{1-6}$ linear or branched alkyl and halogen atoms; f2)

$C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g2) $C_{1-6}$ linear or branched alkyl, optionally substituted by one $C_{1-8}$ alkoxy group and h2) $C_{3-6}$ cycloalkyl-$C_{0-2}$ alkyl optionally substituted by 1 to 3 substituents selected from the group consisting of OH, $NR_5R_6$, CN, $CF_3$, $C_{1-6}$ linear or branched alkyl and halogen atoms;

$R_{2a}$ is selected from the group consisting of i1) $C_{1-8}$-alkyl optionally substituted with 1, 2 or 3 fluor atoms, j1) $C_{1-8}$ alkoxy-$C_{1-8}$ alkyl and k1) $C_{3-6}$ cycloalkyl-$C_{0-2}$ alkyl wherein the cycloalkyl ring is optionally substituted with 1, 2 or 3 fluor atoms with the proviso that when X is O then $R_{2a}$ is not an isopropyl group;

$R_{3a}$ is selected from the group consisting of l1) $C_{1-8}$-alkyl and m1) benzyl optionally substituted by 1 to 3 substituents selected from the group consisting of $C_{1-4}$-alkyl, MeO, CN and halogen atoms with the proviso that when X is a single bond and $R_{1a}$ is a $C_{5-10}$ heterocyclyl-$C_{0-2}$ alkyl group, $R_{3a}$ is not an ethyl group;

$R_{4a}$ is selected from the group consisting of n1) $C_{1-8}$-alkyl, o1) $C_{3-6}$ cycloalkyl-$C_{0-2}$ alkyl optionally substituted by $C_{1-4}$-alkyl and p1) $C_{1-8}$-alkoxy; and $R_5$ and $R_6$ are independently selected from the group consisting of hydrogen atoms and $C_{1-6}$ linear or branched alkyl groups.

13. A pharmaceutical composition comprising a compound of formula (II) as defined in claim 1 and a pharmaceutically acceptable excipient.

14. A method of (i) treating and/or preventing an obesity-related condition selected from the group consisting of obesity, lipid storage disease, and hyperlipemia in a subject in need thereof, and/or (ii) reducing fat accumulation in a subject which does not suffer from obesity, said method comprising administering to said subject a therapeutically effective amount of a compound of formula (II)

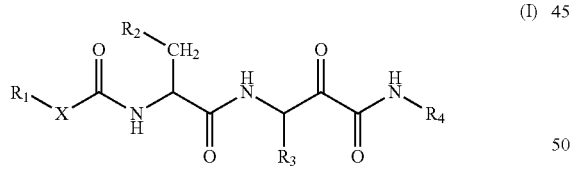

(I)

wherein

X is selected from the group consisting of a single bond, an oxygen atom and a —NH— group;

when X is O, $R_{1a}$ is selected from the group consisting of a1) $C_{1-8}$ alkyl, optionally substituted by one $C_{1-8}$ alkoxy group, b1) $C_{6-10}$ aryl-$C_{1-4}$ alkyl and c1) $C_{5-10}$ heteroaryl-$C_{1-4}$ alkyl wherein the $C_{5-10}$ heteroaryl ring system comprises 1 to 3 heteroatoms selected from the group consisting of nitrogen, oxygen and sulphur, when X is a single bond, $R_{1a}$ is selected from the group consisting of d1) phenyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_5R_6$, CN, $CF_3$, $C_{1-6}$ linear or branched alkyl, $C_{1-6}$ linear or branched alkoxy and halogen atoms; f1) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NH_2$, CN, $CF_3$, $C_{1-6}$ linear or branched alkyl and halogen atoms; g1) $C_{1-6}$ linear or branched alkyl, optionally substituted by one $C_{1-8}$ alkoxy group; and h1) $C_{3-6}$ cycloalkyl-$C_{0-2}$ alkyl optionally substituted by 1 to 3 substituents selected from the group consisting of OH, $NR_5R_6$, CN, $CF_3$, $C_{1-6}$ linear or branched alkyl and halogen atoms;

when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NH_2$, CN, $CF_3$, $C_{1-6}$ linear or branched alkyl and halogen atoms; f2) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g2) $C_{1-6}$ linear or branched alkyl, optionally substituted by one $C_{1-8}$ alkoxy group and h2) $C_{3-6}$ cycloalkyl-$C_{0-2}$ alkyl optionally substituted by 1 to 3 substituents selected from the group consisting of OH, $NR_5R_6$, CN, $CF_3$, $C_{1-6}$ linear or branched alkyl and halogen atoms;

$R_{2a}$ is selected from the group consisting of ii) $C_{1-8}$-alkyl optionally substituted with 1, 2 or 3 fluor atoms, j1) $C_{1-8}$ alkoxy-$C_{1-8}$ alkyl, and k1) $C_{3-6}$ cycloalkyl-$C_{0-2}$ alkyl, wherein the cycloalkyl ring is optionally substituted with 1, 2 or 3 fluor atoms, with the proviso that when X is 0 then $R_{2a}$ is not an isopropyl group;

$R_{3a}$ is selected from the group consisting of l1) $C_{1-8}$-alkyl and m1) benzyl optionally substituted by 1 to 3 substituents selected from the group consisting of $C_{1-4}$-alkyl, MeO, CN and halogen atoms, with the proviso that when X is a single bond and $R_{1a}$ is a $C_{5-10}$ heterocyclyl-$C_{0-2}$ alkyl group, $R_{3a}$ is not an ethyl group;

$R_{4a}$ is selected from the group consisting of n1) $C_{1-8}$-alkyl, o1) $C_{3-6}$ cycloalkyl-$C_{0-2}$ alkyl optionally substituted by $C_{1-4}$-alkyl and p1) $C_{1-8}$-alkoxy; and $R_5$ and $R_6$ are independently selected from the group consisting of hydrogen atoms and $C_{1-6}$ linear or branched alkyl groups;

or a pharmaceutically acceptable salt thereof.

15. The method of claim 14, wherein:

X is selected from the group consisting of a single bond, an oxygen atom and a —NH— group, when X is O, $R_{1a}$ is selected from the group consisting of a1) $C_{1-8}$ alkyl, b1) $C_{6-10}$ aryl-$C_{1-4}$alkyl and c1) $C_{5-10}$ heteroaryl-$C_{1-4}$ alkyl wherein the $C_{5-10}$ heteroaryl ring system comprises 1 to 3 heteroatoms selected from the group consisting of nitrogen, oxygen and sulphur, when X is a single bond, $R_{1a}$ is selected from the group consisting of d1) phenyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; e1) naphthyl optionally substituted by 1 to 3 substituents selected from the group consisting of OH, $NR_{5a}R_{6a}$, CN, $CF_3$, $C_{1-6}$ linear or branched alkyl, $C_{1-6}$ linear or branched alkoxy and halogen atoms; f1) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen atoms; g1) $C_{1-6}$ linear or branched alkyl and h1) $C_{3-6}$ cycloalkyl-$C_{0-2}$alkyl optionally substituted by 1 to 3 substituents selected from the group consisting of OH, $NR_{5a}R_{6a}$, CN, $CF_3$, $C_{1-6}$ linear or branched alkyl and halogen atoms;

when X is a —NH— group, $R_{1a}$ is selected from the group consisting of d2) phenyl optionally substituted by 1 to 3 substituents selected from the group consisting of OH, $NH_2$, CN, $CF_3$, $C_{1-6}$ linear or branched alkyl and halogen atoms; e2) naphthyl optionally substituted by 1 to 3 substituents selected from the group consisting of OH, $NR_{5a}R_{6a}$, CN, $CF_3$, $C_{1-6}$ linear or branched alkyl and halogen atoms; f2) $C_{5-10}$ heterocyclyl-$C_{0-2}$ alkyl wherein the heterocyclyl ring system comprises 1 to 3 heteroatoms selected from the group consisting of nitrogen, oxygen and sulphur and is optionally substituted by 1 to 3 substituents selected from the group consisting of OH, $NR_{5a}R_{6a}$, CN, $CF_3$, $C_{1-6}$ linear or branched alkyl and halogen atoms; g2) $C_{1-6}$ linear or branched alkyl and h2) $C_{3-6}$ cycloalkyl-$C_{0-2}$ alkyl optionally substituted by 1 to 3 substituents selected from the group consisting of OH, $NH_2$, CN, $CF_3$, $C_{1-6}$ linear or branched alkyl and halogen atoms;

$R_{2a}$ is selected from the group consisting of ii) $C_{1-8}$ alkyl, j1) $C_{1-8}$ alkoxy-$C_{1-8}$ alkyl and k1) $C_{3-6}$ cycloalkyl-$C_{0-2}$ alkyl with the proviso that when X is 0 then $R_{2a}$ is not an isopropyl group;

$R_{3a}$ is selected from the group consisting of l1) $C_{1-8}$ alkyl and m1) benzyl optionally substituted by 1 to 3 substituents selected from the group consisting of $C_{1-4}$-alkyl, MeO, CN and halogen atoms with the proviso that when X is a single bond and $R_{1a}$ is a $C_{5-10}$ heterocyclyl-$C_{0-2}$ alkyl group, $R_{3a}$ is not an ethyl group;

$R_{4a}$ is selected from the group consisting of n1) $C_{1-8}$ alkyl and o1) $C_{3-6}$ cycloalkyl-$C_{0-2}$ alkyl optionally substituted by $C_{1-4}$ alkyl; and $R_{5a}$ and $R_{6a}$ are independently selected from the group consisting of hydrogen atoms and $C_{1-6}$ linear or branched alkyl groups;

or a pharmaceutically acceptable salt thereof.

16. The method of claim 14, wherein either (i) X is selected from the group consisting of O and NH and $R_{1a}$ is selected from the group consisting of a1) $C_{1-6}$ alkyl or ii) X is a single bond and the $R_{1a}$ group is selected from the group consisting of d1) phenyl optionally substituted by 1 to 3 substituents selected from the group consisting of CN, $CF_3$, $C_{1-3}$ linear or branched alkyl; and halogen atoms and f1) $C_{5-10}$ heterocyclyl wherein the heterocyclyl ring system is heteroaromatic and comprises 1 to 3 heteroatoms selected from the group consisting of nitrogen, oxygen and sulphur and is optionally substituted by 1 to 3 substituents selected from the group consisting of OH, $NR_5R_6$, CN, $CF_3$, $C_{1-6}$ linear or branched alkyl and halogen.

17. The method of claim 16, wherein X is a single bond.

18. The method of claim 14, wherein the $R_{2a}$ group is selected from the group consisting of $C_{2-5}$ linear or branched alkyl and $C_{3-5}$ cycloalkyl with the proviso that when X is 0 then $R_{2a}$ is not an isopropyl group.

19. The method of claim 14, wherein the $R_{2a}$ group is selected from the group consisting of isopropyl, propyl and cyclopropyl, with the proviso that when X is O then $R_{2a}$ is not an isopropyl group.

20. The method of claim 14, wherein the $R_{3a}$ group is benzyl optionally substituted by 1 to 3 substituents selected from the group consisting of $C_{1-4}$-alkyl, MeO, CN and halogen atoms.

21. The method of claim 14, wherein the $R_{3a}$ group is benzyl optionally substituted by 1 to 3 substituents selected from the group consisting of $C_{1-4}$ alkyl, MeO, CN and halogen atoms; and wherein the $R_{2a}$ group is selected from the group consisting of isopropyl, propyl and cyclopropyl, with the proviso that when X is O then $R_{2a}$ is not an isopropyl group.

22. The method of claim 14, wherein the $R_{4a}$ group is selected from the group consisting of $C_{2-5}$ linear or branched alkyl and $C_{3-5}$ cycloalkyl, both optionally substituted by $C_{1-4}$-alkyl.

23. The method of claim 22, wherein the $R_{4a}$ group is selected from the group consisting of ethyl, tert-butyl and cyclopropyl.

24. The method of claim 14, wherein formula (II) is N-[(1S)-1-(1-benzyl-2-methoxycarbamoyl-2-oxo-ethylcarbamoyl)-3-methyl-butyl]-3-methoxy-benzamide.

* * * * *

UNITED STATES PATENT AND TRADEMARK OFFICE
CERTIFICATE OF CORRECTION

Page 1 of 1

PATENT NO. : 10,294,269 B2
APPLICATION NO. : 15/509107
DATED : May 21, 2019
INVENTOR(S) : Jesús Llenas Calvo et al.

It is certified that error appears in the above-identified patent and that said Letters Patent is hereby corrected as shown below:

In the Claims

Column 57, Lines 43-52 change:

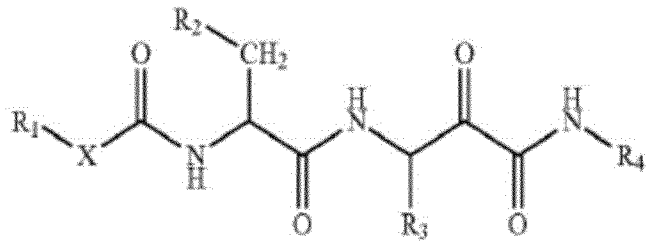

(I)

To:

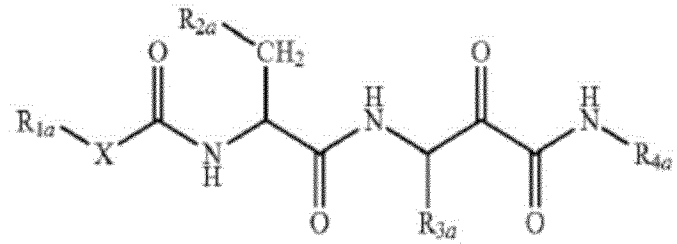

(II)

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*